(12) United States Patent
Alvaro

(10) Patent No.: US 7,196,077 B2
(45) Date of Patent: Mar. 27, 2007

(54) TACHYKININ ANTAGONISTS

(75) Inventor: Giuseppe Alvaro, Verona (IT)

(73) Assignee: Glaxo Group Limited (GB)

( * ) Notice: Subject to any disclaimer, the term of this patent is extended or adjusted under 35 U.S.C. 154(b) by 323 days.

(21) Appl. No.: 10/473,195

(22) PCT Filed: Apr. 5, 2002

(86) PCT No.: PCT/GB02/01601

§ 371 (c)(1),
(2), (4) Date: Feb. 26, 2004

(87) PCT Pub. No.: WO02/081457

PCT Pub. Date: Oct. 17, 2002

(65) Prior Publication Data
US 2004/0127485 A1    Jul. 1, 2004

(30) Foreign Application Priority Data
Apr. 5, 2001 (GB) .................. 0108595.0

(51) Int. Cl.
A61P 25/00 (2006.01)
A61K 31/55 (2006.01)
C07D 243/08 (2006.01)

(52) U.S. Cl. .................. 514/218; 540/575
(58) Field of Classification Search .............. 514/218; 540/575
See application file for complete search history.

(56) References Cited

U.S. PATENT DOCUMENTS

| 4,045,433 A | 8/1977 | Rohricht et al. ......... 260/239.3 |
| 5,719,147 A | 2/1998 | Dorn et al. ............... 514/227.5 |
| 6,642,240 B2 | 11/2003 | Alvaro et al. .......... 514/255.03 |

FOREIGN PATENT DOCUMENTS

| EP | 0899264 B1 | 3/1999 |
| WO | WO 01/25219 | 4/2001 |
| WO | WO 02/32867 | 4/2002 |

OTHER PUBLICATIONS

Severini et al., The Tachykinin Peptide Family, Pharmacological Reviews, vol. 54, No. 2, pp. 285-322, Jun. 2002.*
Armour, D.R., et al. "1,4-benzodiazepin-2-one derived neurokinin-1 receptor antagonists." Bioorganic & Medicinal Chemistry Letters, Oxford, GB, vol. 7, No. 15, Aug. 5, 1997, pp. 2037-2042.
Argyropoulos, et al.; Exp. Opin. Invest. Drugs; 2000; 9/8; 1871-1875.
Ballard, et al.; European Journal of Pharmacology; 2001; 412; 255-264.
Ferraguti et al.; Mol Cell. Neurosci.; 1994; 5:269-276.
Kramer et al.; Science; 1998; 281; 1640-1645.

* cited by examiner

Primary Examiner—Brenda Coleman
(74) Attorney, Agent, or Firm—Lorie A. Morgan

(57) ABSTRACT

The present invention relates to diazepine derivatives of formula (I)

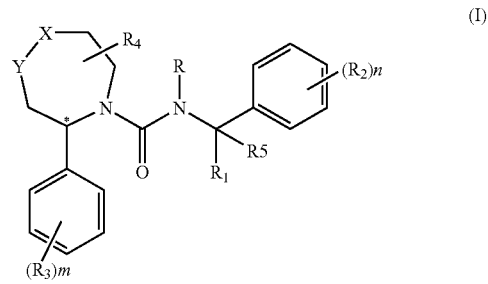

wherein
R represents hydrogen or $C_{1-4}$ alkyl;
$R_1$ represents hydrogen or $C_{1-4}$ alkyl;
$R_2$ represents trifluoromethyl, $C_{1-4}$ alkyl, $C_{1-4}$ alkoxy, trifluoromethoxy or halogen;
$R_3$ represents halogen or $C_{1-4}$ alkyl;
$R_4$ represents hydrogen, halogen, $C_{1-4}$ alkyl or $COR_6$;
$R_5$ represents hydrogen, $C_{1-4}$ alkyl or $R_5$ together within the $R_1$ represents $C_{3-7}$ cycloalkyl;
$R_6$ represents hydroxy, amino, methylamino, dimethylamino, 5 membered heteroaryl group containing 1 to 3 heteroatoms selected independently from oxygen, sulphur and nitrogen or a 6 membered heteroaryl group containing 1 to 3 nitrogen atoms;
m or n are independently zero or an integer from 1 to 3;
X and Y are independently $NR_7$ or methylene;
provided that when X is $NR_7$, Y is methylene and when X is methylene, Y is $NR_7$;
$R_7$ represents hydrogen, $C_{1-4}$ alkyl or $C_{3-7}$ cycloalkyl;
and pharmaceutically acceptable salts and solvates thereof; to process for their preparation and their use in the treatment of condition mediated by tachykinins.

8 Claims, No Drawings

TACHYKININ ANTAGONISTS

CROSS REFERENCES TO RELATED APPLICATIONS

This application is a 371 Application of PCT/GB02/01601, filed 5 Apr. 2002, which claims priority to GB Application Serial No. 0108595.0, filed 5 Apr. 2001.

The present invention relates to diazepine derivatives, to processes for their preparation, to pharmaceutical compositions containing them and to their medical use.

In particular the invention relates to novel compounds, which are antagonists of tachykinins, including substance P and other neurokinins.

Tachykinins are a family of peptides that share a common carboxyl-terminal sequence (Phe-X-Gly-Leu-Met-NH2). They are actively involved in the physiology of both lower and advanced lifeforms. In mammalian lifeforms the main tachykinins are substance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1 (SP-preferring), NK2 (NKA-preferring) and NK3 (NKB-preferring) which are widely distributed throughout the central nervous (CNS) and peripheral nervous system.

Thus the present invention provides compounds of formula (I)

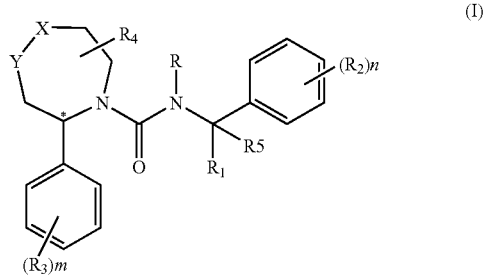

wherein
R represents hydrogen or $C_{1-4}$ alkyl;
$R_1$ represents hydrogen or $C_{1-4}$ alkyl;
$R_2$ represents trifluoromethyl, $C_{1-4}$ alkyl, $C_{1-4}$ alkoxy, trifluoromethoxy or halogen;
$R_3$ represents halogen or $C_{1-4}$ alkyl;
$R_4$ represents hydrogen, halogen, $C_{1-4}$ alkyl or $C(O)R_6$;
$R_5$ represents hydrogen, $C_{1-4}$ alkyl or $R_5$ together within the $R_1$ represents $C_{3-7}$ cycloalkyl;
$R_6$ represents hydroxy, amino, methylamino, dimethylamino, 5 membered heteroaryl group containing 1 to 3 heteroatoms selected independently from oxygen, sulphur and nitrogen or a 6 membered heteroaryl group containing 1 to 3 nitrogen atoms;
m or n are independently zero or an integer from 1 to 3;
X and Y are independently $NR_7$ or methylene;
$R_7$ represents hydrogen, $C_{1-4}$ alkyl or $C_{3-7}$ cycloalkyl;
provided that when X is $NR_7$, Y is methylene and when X is methylene, Y is $NR_7$;

and pharmaceutically acceptable salts and solvates thereof.

A further embodiment of the invention provides compounds of formula (I) and pharmaceutically acceptable salts and solvates thereof wherein
R represents hydrogen or $C_{1-4}$ alkyl;
$R_1$ represents hydrogen or $C_{1-4}$ alkyl;
$R_2$ represents trifluoromethyl, $C_{1-4}$ alkyl, $C_{1-4}$ alkoxy, trifluoromethoxy or halogen;
$R_3$ represents halogen or $C_{1-4}$ alkyl;
$R_4$ represents hydrogen, halogen or a $C_{1-4}$ alkyl group;
$R_5$ represents hydrogen;
m or n are independently zero or an integer from 1 to 3;
X and Y are independently $NR_7$ or methylene;
$R_7$ represents hydrogen, $C_{1-4}$ alkyl or $C_{3-7}$ cycloalkyl;
provided that when X is $NR_7$, Y is methylene and when X is methylene, Y is $NR_7$;

and pharmaceutically acceptable salts and solvates thereof.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, trifluoroacetates, acetates, citrates, succinates, tartrates, fumarates and maleates.

The solvates may, for example, be hydrates.

References hereinafter to a compound according to the invention include both compounds of formula (I) and their pharmaceutically acceptable acid addition salts and their pharmaceutically acceptable solvates.

It will be appreciated by those skilled in the art that the compounds of formula (I) contain at least one chiral centre (namely the carbon atom shown as * in formula (I)) and may be represented by formula (1a) and (1b).

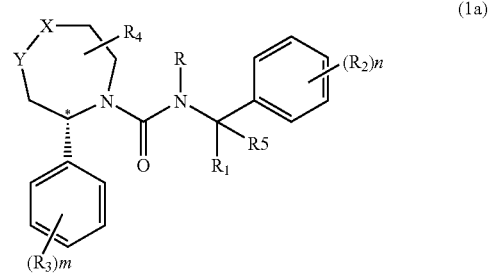

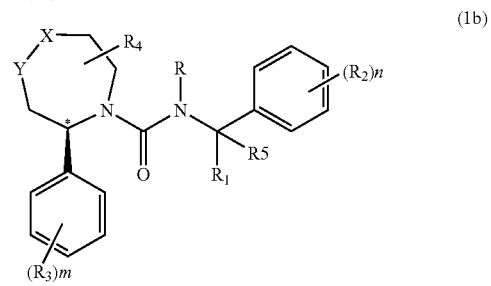

The wedge bond indicates that the bond is above the plane of the paper. The broken bond indicates that the bond is below the plane of the paper.

The configuration shown for the chiral carbon indicated as * in formula (1a) is α and in formula(1b) is β.

In general in the specific compounds named below, when Y means $NR_7$ and X means methylene the α configuration at the chiral atom indicated by * corresponds to the R isomer and the β configuration corresponds to the S isomer.

When X means $NR_7$ and Y means methylene the a configuration at the chiral atom indicated by * corresponds to the S isomer and the β configuration corresponds to the R isomer.

The assignment of the R and S configuration of the asymmetric carbon atoms of the compounds of the invention has been made according to the rules of Cahn, Ingold and Prelog 1956, 12, 81.

It is to be understood that all stereoisomeric forms including all enantiomers and mixtures thereof are encompassed within the scope of the present invention and the reference to compound of formula (I) include all stereisomeric forms unless otherwise stated.

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl, tert-butyl, 1 methylethyl or 2-methyl propyl.

The term halogen refers to fluorine, chlorine, bromine or iodine.

The term $C_{1-4}$ alkoxy group may be a straight chain or a branched chain alkoxy group, for example methoxy, ethoxy, propoxy, prop-2-oxy, butoxy, but-2-oxy or methylprop-2-oxy.

The term $C_{3-7}$ cycloalkyl group means a non aromatic monocyclic hydrocarbon ring of 3 to 7 carbon atom such as, for example, cyclopropyl, cyclobutyl, cyclopentyl, cyclohexyl or cycloheptyl.

The term 5 or 6 membered heteroaryl group according to the invention includes furanyl, thiophenyl, pyrrolyl, imidazolyl, thiazolyl, oxazolyl, pyrazolyl, isoxazolyl, isothiazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl or 1,3,5-triazinyl and the like.

In the compounds of formula (I) wherein Y is $NR_7$ and X is methylene(1c), the group $R_4$ may be in position 3, 5, 6, 7 of the diazepine ring;

In the compounds of formula (I) wherein Y is methylene and X is $NR_7$ (1d), the group $R_4$ may be in position 2, 3, 5, 6 of the diazepine ring.

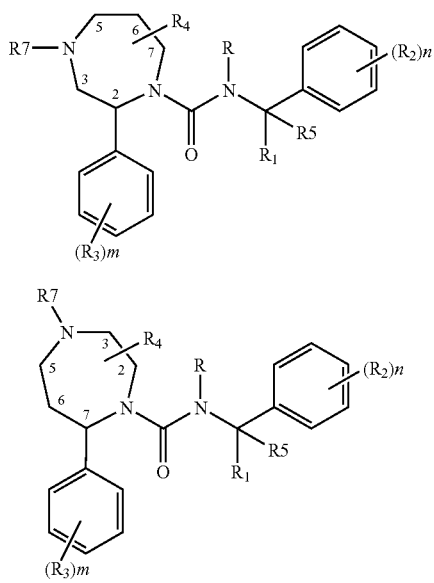

R is preferably hydrogen or methyl.
$R_1$ is preferably hydrogen or methyl.
$R_2$ is preferably trifluoromethyl, methyl, chlorine or fluorine atom and n is preferably an integer from 1 to 2.
$R_3$ is preferably halogen (e.g. fluorine) and/or a $C_{1-4}$ alkyl (e.g. methyl) group and m is preferably an integer from 1 to 2.
$R_4$ is preferably hydrogen, halogen (e.g. fluorine), methyl or $C(O)R_6$.
$R_5$ is preferably hydrogen, methyl or together with $R_1$ is cyclopropyl.
$R_6$ is preferably amino, methylamino or dimethylamino.
$R_7$ is preferably hydrogen, methyl or cyclopropyl.

A preferred class of compounds of formula (I) is that wherein the chiral atom indicated as * is in β configuration.

For compounds of formula (I) m is conveniently 2 and within these compounds those wherein the groups $R_3$ are at the 2 and the 4 position of the phenyl ring are preferred.

A further preferred class of compounds of formula (I) is that wherein $R_2$ is trifluoromethyl and/or halogen (i.e chlorine or fluorine), $R_3$ is halogen (e.g. fluorine) and $C_{1-4}$ alkyl (e.g. methyl) group at the 2 and the 4 position of the phenyl ring, X is $NH_2$ and Y is methylene or Y is $NH_2$ and X is methylene, $R_1$ is a methyl or hydrogen, R is methyl, $R_5$ and $R_4$ are hydrogen m is 2 and n is 1 or 2.

Preferred compounds according to the invention are:

2-(S)-(4-Fluoro-2-methyl-phenyl)-[1,4]-diazepane-1-carboxylic acid, (3,5-bis-trifluoromethyl-benzyl)-methylamide;

7-(R)-(4-Fluoro-2-methyl-phenyl)-[1,4]-diazepane-1-carboxylic acid, (3,5-bis-trifluoromethyl-benzyl)-methylamide;

2-(S)-(4-Fluoro-2-methyl-phenyl)-[1,4]-diazepane-1-carboxylic acid, [1-(R)-(3,5-bis-trifluoromethyl-phenyl)-ethyl]-methylamide;

7-(R)-(4-Fluoro-2-methyl-phenyl)[1,4]-diazepane-1-carboxylic acid, [1-(R)-(3,5-bis-trifluoromethyl-phenyl)-ethyl]-methylamide;

2-(S)-(4-Fluoro-2-methyl-phenyl)-[1,4]-diazepane-1-carboxylic acid, (3,5-dichloro-benzyl)-methylamide;

7-(R)-(4-Fluoro-2-methyl-phenyl)-[1,4]-diazepane-1-carboxylic acid, (3,5-dichloro-benzyl)-methylamide;

2-(S)-(4-Fluoro-2-methyl-phenyl)-[1,4]-diazepane-1-carboxylic acid, [1-(S)-(3,5-bis-trifluoromethyl-phenyl)-ethyl]-methylamide;

7-(R)-(4-Fluoro-2-methyl-phenyl)-[1,4]-diazepane-1-carboxylic acid, [1-(S)-(3,5-bis-trifluoromethyl-phenyl)-ethyl]-methylamide;

2-(S)-(4-Fluoro-2-methyl-phenyl)-[1,4]-diazepane-1-carboxylic acid, (3-chloro-4-fluoro-benzyl)-methylamide;

7-(R)-(4-Fluoro-2-methyl-phenyl)-[1,4]-diazepane-1-carboxylic acid, (2,5-dichloro-benzyl)-methylamide;

2-(S)-(4-Fluoro-phenyl)-[1,4]-diazepane-1-carboxylic acid, (3,5-bis-trifluoromethyl-benzyl)-methylamide;

7-(R)-(4-Fluoro-phenyl)-[1,4]-diazepane-1-carboxylic acid, (3,5-bis-trifluoromethyl-benzyl)-methylamide;

7-(R)-(4-Fluoro-2-methyl-phenyl)-4-methyl-[1,4]-diazepane-1-carboxylic acid, (3,5-dichloro-benzyl)-methylamide;

7-(R)-(4-Fluoro-2-methyl-phenyl)-4-methyl-[1,4]-diazepane-1-carboxylic acid, (3,5-bis-trifluoronethyl-benzyl)-methylamide; and 7-(R)-(4-Fluoro-2-methyl-phenyl)-4-methyl-[1,4]-diazepane-1-carboxylic acid, [1-(R)-(3,5-bis-trifluoromethyl-phenyl)-ethyl]-methylamide;

and pharmaceutically acceptable salts and solvates thereof.

The compounds of the invention are antagonists of tachykinins, including substance P and other neurokinins, both in vitro and in vivo and are thus of use in the treatment of conditions mediated by tachykinins, including substance P and other neurokinins.

The compounds of the present invention may also have activity as serotonin reuptake inhibitors.

$NK_1$-receptor binding affinity has been determined in vitro by the compounds' ability to displace [3H]-substance P (SP) from recombinant human $NK_1$ receptors expressed in Chinese Hamster Ovary (CHO) cell membranes.

CHO cell membranes were prepared by using a modification of the method described by Dam T and Quirion R (Peptides, 7: 855–864, 1986). Thus ligand binding was performed in 0.4 mL of 50 mM HEPES, pH 7.4, containing 3 mM $MnCl_2$, 0.02% BSA, 0.5 nM [$^3$H]-Substance P (30÷56 Ci/mmol, Amersham), a final membrane concentration of 25 μg of protein/ml, and the test compounds. The incubation proceeded at room temperature for 40 min. Non-specific binding was determined using excess of Substance P (1 μM) and represents about 6% of the total binding.

Compounds of the invention were further characterised in a functional assay for the determination of their inhibitory effect. Human-$NK_1$-CHO cells were stimulated with Substance P and the receptor activation was evaluated by measuring the accumulation of cytidinediphosphodiacylglycerol (CDP-DAG), which is the liponucleotide precursor of phosphatidylinositol diphosphate. CDP-DAG accumulates in the presence of $Li^+$ as a consequence of the receptor mediated activation of phospholipase C (PLC) (Godfrey, Biochem. J., 258: 621–624, 1989). The method is described in detail by Ferraguti et al. (Mol. Cell. Neurosci., 5: 269–276, 1994).

The action of the compounds of the invention at the $NK^1$ receptor may be determined by using conventional tests. Thus the ability to bind at the $NK_1$ receptor was determined using the gerbil foot tapping model as described by Rupniak & Williams, Eur. J. of Pharmacol., 1994.

Human Serotonin Transporter (hSERT) binding affinity has been determined in vitro by the compounds' ability to displace [$^3$H]-Imprarmine from human serotonin transporter expressed in Human Embryonic Kidney HEK293 cell membranes (Receptor Biology Inc.). For the binding reaction, 4 nM of [$^3$H]-Imipramine (703 GBq/mmol, Amersham) were incubated with 0.02 mg/ml of cell membrane and the compound to be tested at different concentrations (7 concentration points) in 50 mM Tris HCl, pH 7.5, 120 mM of NaCl and 5 mM KCl. The reaction was performed for 60 min at 4° C. and was terminated by filtration through GF/B Unifilters 96 wells/case (presoaked in 0.5% PEI) using a Cell Harvester (Packard). Scintillation fluid was added to each filtered spot and radioactivity was determined using a scintillation counter (TopCount (Packard)). Non-specific binding was determined using Imipramine (100 μM) and represents about 5% of the total binding.

Competition experiments were conducted with duplicate determination for each point. Msat601 software package was used to elaborate the competition binding data. $IC_{50}$ values were converted to $K_i$ values using Cheng-Prusoff equation.

Compounds of the invention are useful in the treatment of CNS disorders and psychotic disorders, in particular in the treatment or prevention of depressive states and/or in the treatment of anxiety.

Depressive states include major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamrines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are useful as analgesics. In particular they are useful in the treatment of traumatic pain such as postoperative pain; traumatic avulsion pain such as brachial plexus; chronic pain such as artritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; bums; scar pain; itch; and thalamic pain such as post stroke thalamic pain.

Compounds of the invention are also useful in the treatment of sleep disorders including dysomnia, insomnia, sleep apnea, narcolepsy, and circadian ritmic disorders.

Compounds of the invention are also useful in the treatment or prevention of the cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer, poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention have been found to exhibit anxiolytic activity in conventional tests. For example in marmoset human threat test (Costall et al., 1988).

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected. Thus for parenteral administration a daily dose will typically be in the range of 1 to about 100 mg, preferably 1 to 80 mg per day. For oral administration a daily dose will typically be within the range 1 to 300 mg e.g 1 to 100 mg.

Compounds of formula (I), and salts and solvates thereof, may be prepared by the general methods outlined hereinafter. In the following description, the groups X, Y, R, $R_1$, $R_2$, $R_3$, $R_4$, $R_5$ $R_6$ $R_7$, m and n have the meaning as previously defined for compounds of formula (I) unless otherwise stated.

Compounds of formula (I), wherein Y is methylene and X is $NR_7$, may be prepared by reduction of compounds of formula (II)

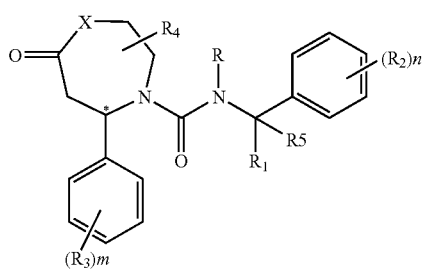

(II)

Compounds of formula (I), wherein Y is $NR_7$ and X is methylene, may be prepared by reduction of compounds of formula (III)

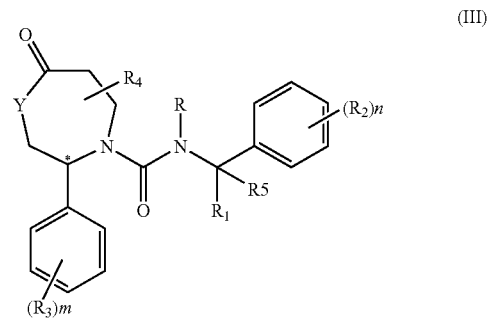

(III)

The reduction is carried out with a suitable metal reducing agent such as a metal hydride, at a temperature within the range of room temperature to the reflux temperature of the reaction mixture.

The reaction conveniently takes place in an aprotic solvent such as dicholoromethane, 1,2 dichloroethane, acetone, or an ether such as tetrahydrofuran.

Example of suitable metal hydrides for this reaction include borane hydride, alane hydride or a metal hydride complex like lithium aluminium hydride or sodium borohydride, or an organometallic complex such as borane-methyl sulphide, 9-borabicyclononane (9-BBN), triethylsilane, sodium triacetoxyborohydride, sodium cyanoborohydride. suitable solvents for the reaction are ether (e.g. tetrahydrofuran), or halohydrocarbon (e.g. dichloromethane) or an amide (e.g. N,N-dimethylformamide).

Compounds of formula (II) and (III), wherein $R_7$ is hydrogen, may be prepared by Beckmann rearrangement of oxime derivatives of formulae (IV) and (V) respectively,

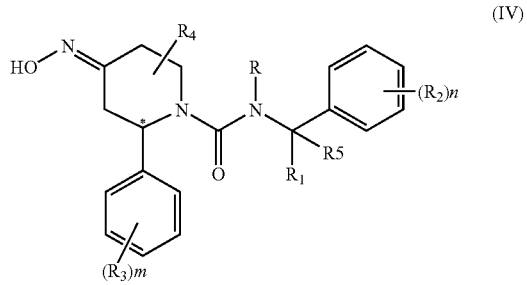

(IV)

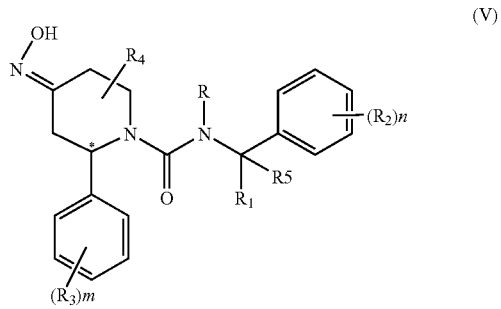

(V)

in the presence of tosyl chloride and an inorganic base such as sodium carbonate. The reaction may be carried out in an aprotic organic solvent such as acetone, at a temperature within the range of room temperature to the reflux temperature of the reaction mixture.

The oximes (IV) and (V) may be prepared by treating compounds of formula (VI)

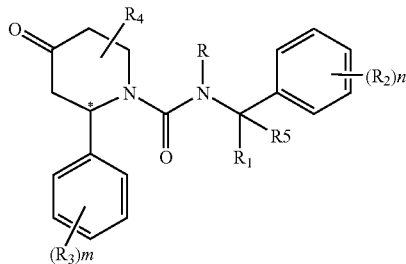

(VI)

with hydroxylamine in a protic solvent such as methanol.

Compounds of formulae (II) or (III) wherein $R_7$ is $C_{1-4}$ alkyl or $C_{3-7}$ cycloalkyl may be prepared from compounds of formulae (II) or (III) wherein R5 is hydrogen by reaction with an alkylating agent $R_7X$ wherein X is a suitable leaving group such chloride, bromide, triflate, mesylate or tosylate.

Compounds of formula (VI) may be prepared by treating tetrahydro-4-pyridone compounds of formula (VII)

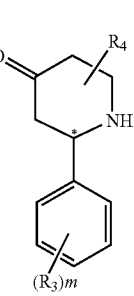

(VII)

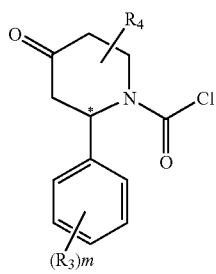

(VIII)

with triphosgene in an aprotic solvent such as dichloromethane and in the presence of an organic base such as triethylamine to form the intermediate carbonyl chloride (VIII), which may be isolated if required, followed by reaction of compound (VIII) with the amino compound (IX).

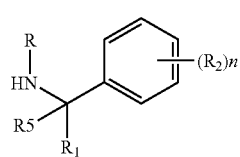

(IX)

The reaction conveniently take place in an aprotic solvent such as a hydrocarbon, a halohydrocarbon such as dichloromethane or an ether such as tetrahydrofuran optionally in the presence of a base such as a tertiary amine e.g. diisopropylethylamine.

Where it is desired to isolate a compound formula (I) as a salt thereof, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compound of formula (I) using conventional methods.

Compounds of formula (VII), (VIII) and (IX) may be prepared by analogous methods to those used for known compounds.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of compounds of formula (I) using conventional methods.

Thus, for example, specific enantiomers of the compounds of formula (I) may be obtained from corresponding enantiomeric mixture of a compound of formula (I) using chiral HPLC procedure.

Alternatively, enantiomers of a compound of general formula (I) may be synthesised from the appropriate optically active intermediates using any of the general processes described herein.

Thus for example the required enantiomer may be prepared by the corresponding chiral tetrahydro-4-pyridone of formula (VII) using any of the processes described above for preparing compounds of formula (I) from compounds of formula (VII).

The chiral compounds (VII) may be prepared from the corresponding racemic (VII) using conventional procedures such as salt formation with a suitable optically active acid, separating the resultant diastereoisomeric salts by conventional means e.g. chromatography and crystallisation followed by hydrolysis of the diastereoisomeric salts. A suitable optically active acid for use in the process is L-(+)-mandelic acid.

In a further embodiment of the invention the enantiomers of the compound of formula (IX) may be prepared by reaction of a chiral amine (IX) using any of the process described above for preparing compounds of formula (VII) from amine (IX).

The chiral amine (IX) may be prepared from the corresponding racemic amine (VII) using any conventional procedures such as salt formation with a suitable optically active acid. A suitable optically active acid for use in the process is L-(+)-mandelic acid.

The invention is further illustrated by the following Intermediates and Examples which are not intended as a limitation of the invention.

In the Intermediates and Examples unless otherwise stated:

Melting points (m.p.) were determined on a Buchi m.p. apparatus and are uncorrected. R.T. or r.t. refer to room temperature.

Infrared spectra (IR) were measures in chloroform or nujol solutions on a FT-IR instrument. Proton Magnetic Resonance (NMR) spectra were recorded on Varian instruments at 400 or 500 MHz, chemical shifts are reported in ppm (δ) using the residual solvent line as internal standard. Splitting patterns are designed as s, singlet; d, double; t, triple; q, quartet; m, multiplet; b, broad. Mass spectra (MS) were taken on a VG Quattro mass spectrometer. Optical rotations were determined at 20 C. with a Jasco DIP360 instrument (1=10 cm, cell volume=1 mL, λ=589 nm). Flash silica gel chromatography was carried out over silica gel 230–400 mesh supplied by Merck AG Darmstadt, Germany. T.l.c. refers to thin layer chromatography on 0.25 mm silica gel plates (60F-254 Merck) and visualized with UV light.

Solutions were dried over anhydrous sodium sulphate.

Methylene chloride was redistilled over calcium hydride and tetrahydrofuran was redistilled over sodium.

The following abbreviation are used in the text: AcOEt=ethyl acetate, CH=cyolohexane, DCM=methylene chloride, DIPEA=N,N-diisopropylethylamine, DMF=NN'-dimethylformamide, Et2O=diethyl ether, EtOH=ethanol, McOH=methanol TEA=triethylamine, TBF=tetrahydrofuran.

Intermediate 1

1-(Benzyloxycarbonyl)-2-(4-fluoro-2-methyl-phenyl)-2,3-dihydro-4-pyridone

A small amount of iodine was added to a suspension of magnesium turnings (13.2 g) in dry TVF (300 mL), at r.t., under a Nitrogen atmosphere, then the mixture was vigorously refluxed for 20 minutes. To this suspension, a 15% of a solution of 2-bromo-5-fluoro-toluene (52.5 mL) in anhydrous THF (300 mL) was added. The suspension was heated under vigorous reflux until the brown colour disappeared. The remaining part of the bromide solution was added dropwise over 1 hour to the refluxing suspension which was then stirred for a further 1 hour. This solution of Grignard reagent was then added drop-wise to the pyridinium salt obtained from benzyl chloroformate (48.7 mL) and 4-methoxypyridine (25 mL) in dry THF (900 mL) at −23° C.

The obtained solution was stirred 1 hour at −20° C. then it was warmed up to 20° C., a 10% hydrochloric acid solution (560 mL) was added and the aqueous layer was extracted with AcOEt (2×750 mL).

The combined organic extracts were washed with 5% sodium hydrogen carbonate solution (600 mL) and brine (600 mL) then partially concentrated in vacuo.

CH (400 mL) was added drop-wise over 1 hour at 20° C. and the resulting mixture was stirred 30 minutes and then filtered to give the title compound as a white solid (66 g).

IR (nujol, cm$^{-1}$): 1726 and 1655 (C=O), 1608 (C=C).

NMR (d$_6$-DMSO): δ (ppm) 8.19 (d, 1H); 7.31–7.18 (m, 5H); 7.08 (m, 2H); 6.94 (dt, 1H); 5.77 (d, 1H); 5.36 (d, 1H); 5.16 (2d, 2H); 3.26 (dd, 1H); 2.32 (d, 1H); 2.26 (s, 3H).

MS (ES/+): m/z=340 [MH]$^+$.

Intermediate 2

2-(4-Fluoro-2-methyl-phenyl)-piveridine-4-one

Method A

2-Methyl-4-fluoro-benzaldehyde (4 g) was added to a solution of 4-aminobutyl-2-one ethylene acetal (3.8 g) in dry benzene (50 mL) and the solution was stirred at r.t. under a Nitrogen atmosphere. After 1 hour the mixture was heated at reflux for 16 hours and then allowed to cool to rt. This solution was slowly added to a refluxing solution of p-toluenesulphonic acid (10.6 g) in dry benzene (50 mL) previously refluxed for 1 hour with a Dean-Stark apparatus. After 3.5 hours the crude solution was cooled and made basic with a saturated potassium carbonate solution and taken up with AcOEt (50 mL). The aqueous phase was extracted with AcOEt (3×50 mL) and Et2O (2×50 mL). The organic layer was dried and concentrated in vacuo to a yellow thick oil as residue (7.23 g). A portion of the crude mixture (3 g) was dissolved in a 6N hydrochloric acid solution (20 mL) and stirred at 60° C. for 16 hours. The solution was basified with solid potassium carbonate and extracted with DCM (5×50 mL). The combined organic phases were washed with brine (50 mL), dried and concentrated in vacuo to give the title compound (2.5 g) as a thick yellow oil.

Method B

L-selectride (1M solution in dry TBF, 210 mL) was added drop-wise, over 80 minutes, to a solution of intermediate 1 (50 g) in dfy THF (1065 mL) previously cooled to −72° C. under a Nitrogen atmosphere. After 45 minutes, 2% sodium hydrogen carbonate solution (994 mL) was added drop-wise and the solution was extracted with AcOEt (3×994 mL). The combined organic phases were washed with water (284 mL) and brine (568 mL). The organic phase was dried and concentrated in vacuo to get 1-benzyloxycarbonyl-2-(4-fluoro-2-methyl-phenyl)-piperidine-4-one as a pale yellow thick oil (94 g) which was used as a crude.

This material (94 g) was dissolved in AcOEt (710 mL), then 10% Pd/C (30.5 g) was added under a Nitrogen atmosphere. The slurry was hydrogenated at 1 atmosphere for 30 minutes. The mixture was filtered through Celite and the organic phase was concentrated in vacuo to give the crude 2-(4-fluoro-2-methyl-phenyl)-piperidine-4-one as a yellow oil. This material was dissolved in AcOEt (518 mL) at r.t. and racemic camphorsulphonic acid (48.3 g) was added. The mixture was stirred at r.t for 18 hours, then the solid was filtered off, washed with AcOEt (2×50 mL) and dried in vacuo for 18 hours to give 2-(4-fluoro-2-methyl-phenyl)-piperidine-4-one, 10-camphorsulfonic acid salt as a pale yellow solid (68.5 g). (M.p.: 167–169° C.-NMR (d$_6$DMSO): δ (ppm) 9.43 (bs, 1H); 9.23 (bs, 1H); 7.66 (dd, 1H); 7.19 (m, 2H); 4.97 (bd, 1H); 3.6 (m, 2H); 2.87 (m, 3H); 2.66 (m, 1H); 2.53 (m, 2H); 2.37 (s+d, 4H); 2.22 (m, 1H); 1.93 (t, 1H); 1.8 (m, 2H); 1.26 (m, 2H); 1.03 (s, 3H); 0.73 (s, 3H).

This material (68.5 g) was suspended in AcOEt (480 mL) and stirred with a saturated sodium hydrogen carbonate (274 mL). The organic layer was separated and washed with further water (274 mL). The organic phase was dried and concentrated in vacuo to give the title compound (31 g) as a yellow-orange oil.

NMR (d$_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).

MS (ES/+): m/z=208 [MH]$^+$.

Intermediate 3

2-(4-Fluoro-2-methyl-phenyl)-4-oxo-piperidine-1-carboxylic acid, (3,5-bis-trifluoromethyl-benzyl-methylamide A solution of triphosgene (1.43 g) dissolved in dry DCM (10 mL) was added to a solution of intermediate 2 (2.5 g) and DIPEA (8.4 mL) in dry DCM (20 mL) previously cooled to 0° C. under a Nitrogen atmosphere. The solution was stirred at 0° C. for 2 hours, then (3,5-bis-trifluoromethyl-benzyl)-methylamine hydrochloride (5.63 g) and DIPEA (3.34 mL) were added. The mixture was stirred under nitrogen at r. t. for 14 hours. The mixture was taken up with AcOEt (50 mL), washed with cold 1N hydrochloric acid solution (3×20 mL) and brine (10 mL). The organic layer was dried and concentrated in vacuo to a residue which was purified by flash chromatography (AcOEt/CH 3:7) to give the title compound as a white foam (3.85 g).

IR (nujol, cm$^{-1}$): 1721 and 1641 (C=O).

NMR (d$_6$-DMSO): δ (ppm) 7.96 (s, 1H); 7.76 (s, 2H); 7.25 (dd, 1H); 6.97 (dd, 1H); 6.90 (dt, 1H); 5.22 (t, 1H); 4.59 (d, 1H); 4.43 (d, 1H); 3.63–3.49 (m, 2H); 2.79 (s, 3H); 2.69 (m, 2H); 2.49 (m, 2H); 2.26 (s, 3H).

MS (ES/+): m/z=491 [MH]$^+$.

Intermediate 4

2-(R)-(4-Fluoro-2-methyl-phenyl)-4-oxo-piperidine-1-carboxylic acid, [1-(R)-3,5-bis-trifluoromethyl-phenyl)-ethyl]-methylamide (4a) and 2-(S)-(4-Fluoro-2-methyl-phenyl)-4-oxo-piperidine-1-carboxylic acid, [1-(R)-3,5-bis-trifluoromethyl-phenyl)-ethyl]-methylamide (4b)

Method A

A solution of triphosgene (147 mg) dissolved in dry DCM (5 mL) was added drop-wise to a solution of intermediate 2 (250 mg) and DIPEA (860 μL) in dry DCM (15 mL) previously cooled to 0° C. under a Nitrogen atmosphere. After 2 hours, [1-(R)-3,5-bis-trifluoromethyl-phenyl)-ethyl]-methylamine hydrochloride (503 mg) and DIPEA (320 μL) in dry acetonitrile (20 mL) were added and the mixture was heated to 70° C. for 16 hours. Further [1-(R)-(3,5-bis-trifluoromethyl-phenyl)-ethyl]-methylamine hydrochloride (170 mg) and DIPEA (100 μL) were added and the mixture was stirred at 70° C. for further 4 hours. Next, the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 4a (230 mg) as a white foam,
2. intermediate 4b (231 mg) as a white foam.

Intermediate 4a

NMR (d$_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

Intermediate 4b

NMR (d$_6$-DMSO): δ (ppm) 7.96 (bs, 1H); 7.75 (bs, 2H); 7.24 (dd, 1H); 6.98 (dd, 1H); 6.93 (dt, 1H); 5.29 (q, 1H); 5.24 (t, 1H); 3.56 (m, 1H); 3.48 (m, 1H); 2.70 (s, 3H); 2.50 (m, 4H); 2.26 (s, 3H); 1.54 (d, 3H).

Intermediate 4a

Method B

A saturated sodium hydrogen carbonate solution (324 mL) was added to a solution of intermediate 9 (21.6 g) in AcOEt (324 mL) and the resulting mixture was vigorously stirred for 15 minutes. The aqueous layer was back-extracted with further AcOEt (216 mL) and the combined organic extracts were dried and concentrated in vacuo to give intermediate 8 as a yellow oil, which was treated with TEA (19 mL) and AcOEt (114 mL). The solution obtained was added drop-wise over 40 minutes to a solution of triphosgene (8 g) in AcOEt (64 mL) previously cooled to 0° C. under a Nitrogen atmosphere, maintaining the temperature between 0° C. and 8° C.

After stirring for 1 hours at 0° C. and for 3 hours at 20° C., [1-(R)-(3,5-bis-trifluoromethyl-phenyl)-ethyl]-methylamine hydrochloride (29.7 g), AcOEt (190 mL) and TEA (38 mL) were added to the reaction mixture which was then heated to reflux for 16 hours.

The solution was washed with 10% sodium hydroxide solution (180 mL), 1% hydrochloric acid solution (4×150 mL), water (3×180 mL) and brine (180 mL). The organic layer was dried and concentrated in vacuo to a residue, which was purified through a silica pad (CH/AcOEt 9:1) to give the title compound (21.5 g) as a brown thick oil.

NMR (d$_6$-DMSO): δ (ppm) 7.97–7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

Intermediate 5

2-(S)-(4-Fluoro-2-methyl-phenyl)-4-oxo-piperidine-1-carboxylic acid, [1-(S)-(3,5-bis-trifluoromethyl-phenyl)-ethyl]-methylamide (5a) and 2-(R)-(4-Fluoro-2-methyl-phenyl)-4-oxo-piperidine-1-carboxylic acid, [1-(S)-(3,5-bis-trifluoromethyl-phenyl)-ethyl]-methylamide (5b)

Method A:

A solution of triphosgene (147 mg) dissolved in dry DCM (5 mL) was added to a solution of intermediate 2 (250 mg) and DIPEA (860 μL) in dry DCM (15 mL) previously cooled to 0° C. under a Nitrogen atmosphere. After 2 hours, a solution of [1-(S)-(3,5-bis-trifluoromethyl-phenyl)-ethyl]-methylamine hydrochloride (510 mg) and DIPEA (320 μL) in dry acetonitrile (20 mL) was added and the mixture was heated to 70° C. for 16 hour. Next, further [1-(S)-(3,5-bis-trifluoromethyl-phenyl)-ethyl]-methylamine hydrochloride (170 mg) and DIPEA (105 μL) were added. After further 4 hours at 70° C., the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 5a (234 mg) as a white foam,
2. intermediate 5b (244 mg) as a white foam.

Intermediate 5a

NMR (d$_6$-DMSO): δ (ppm) 7.97–7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

Intermediate 5b

NMR (d$_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

Intermediate 5b

Method B:

A solution of triphosgene (288 mg) dissolved in dry DCM (10 mL) was added to a solution of intermediate 8 (500 mg) and TEA (1.35 mL) in dry DCM (15 mL) previously cooled to 0° C. under a Nitrogen atmosphere. After 2 hours, a solution of [1-(S)-(3,5-bis-trifluoromethyl-phenyl)-ethyl]- methylaniline hydrochloride (1.1 g) and DIPEA (1.7 mL) in dry acetonitrile (20 mL) was added and the mixture was heated to 70° C. for 3 hours. The mixture was allowed to cool to r.t., taken up with AcOEt (50 mL), washed with a 1N hydrochloric acid cold solution (3×20 mL) and brine (2×20 mL). The organic layer was dried and concentrated in vacuo to a residue, which was purified by flash chromatography (CH/AcOEt 8:2) to give the title compound (685 mg) as a white foam.

NMR ($d_6$-DMSO): δ (ppm) 7.96 (s, 1H); 7.75 (s, 2H); 7.24 (dd, 1H); 6.98 (dd, 1H); 6.92 (dt, 1H); 5.29 (q, 1H); 5.24 (t, 1H); 3.55 (m, 1H); 3.47 (m, 1H); 2.7 (s, 3H); 2.6–2.4 (m, 4H); 2.26 (s, 3H); 1.53 (d, 3H).

Intermediate 6

2-(S)-(4-Fluoro-2-methyl-phenyl)-4-oxo-3,4-dihydro-2H-pyridine-1-carboxylic acid, (1R,2S,5R)-2-isopropyl-5-methyl-cyclohexyl ester (6a) and 2-(R)-(4-Fluoro-2-methyl-phenyl)-4-oxo-3,4-dihydro-2H-pyridine-1-carboxylic acid, (1R,2S,5R)-2-isopropyl-5-methyl-cyclohexyl ester (6b)

A solution of 2-bromo-5-fluoro-toluene (3.68 g) in dry THF (10 mL) was dropped over 30 minutes, into a mixture of magnesium (525 mg) and iodine (1 crystal) in dry THF (5 mL) previously heated to 70° C. under a Nitrogen atmosphere. The mixture was stirred at 70° C. for 1.5 hours, then allowed to cool to r.t., A solution of (−)-methyl chloroformate (3.53 mL) in dry THF (15 mL) was added to a solution of 4-methoxypyridine (1.52 mL) in dry THF (35 mL) previously cooled to −78° C. under a Nitrogen atmosphere. After 15 minutes, the solution containing the 4-fluoro-2-methyl-phenyl magnesium bromide was added drop-wise, and the mixture was stirred at −78° C. for 1 hour. The reaction was quenched by the addition of 1M hydrochloric acid solution (20 mL), warmed to r.t. and stirred at 23° C. for 30 minutes. After extraction with AcOEt (2×150 mL), the combined organic extracts were washed with brine (50 mL), dried and concentrated in vacuo to a residue, which was purified by flash chromatography (CH/THF/toluene 8:1:1) to give:
1. intermediate 6a (3.44 g-yellow oil)
2. intermediate 6b (530 mg-white solid).

Intermediate 6a
T.l.c.: CH/THF/toluene 7:2:1, Rf=0.59.
IR (nujol, cm$^{-1}$): 1718 and 1675 (C=O).
NMR ($d_6$-DMSO): δ (ppm) 8.14 (d, 1H); 7.08 (dd, 1H); 7.02 (dd, 1H); 6.95 (m, 1H); 5.68 (d, 1H); 5.34 (d, 1H); 4.47 (m, 1H); 3.26 (dd, 1H); 2.30 (m, 4H); 1.7 (m, 4H); 1.33 (m, 2H); 0.8 (m, 11H).

Intermediate 6b
M.p.: 117–120° C.
T.l.c.: CH/THF/toluene 7:2:1, Rf=0.56.
IR (nujol, cm$^{-1}$): 1718 and 1669 (C=O).
NMR ($d_6$-DMSO): δ (ppm) 8.17 (d, 1H); 7.04–6.94 (m, 3H); 5.70 (d, 1H); 5.35 (d, 1H); 4.42 (m, 1H); 3.26 (dd, 1H); 2.30 (m, 4H); 1.58–1.40 (m, 3H); 1.2–0.7 (m, 8H); 0.51–0.34 (bs, 6H):

Intermediate 7

2-(R)-(4-Fluoro-2-methyl-phenyl)-2,3-dihydro-1H-pyridin-4-one

Sodium methoxide (100 mg) was added to a solution of intermediate 6b (170 mg) in MeOH (15 mL) under a Nitrogen atmosphere. The mixture was refluxed for two hours, and the solvent was removed in vacuo. The residue was partitioned between water (10 mL) and AcOEt (15 mL). The layers were separated, and the aqueous phase was extracted with further AcOEt (4×10 mL). The combined organic extracts were washed with brine (10 mL), dried and concentrated in vacuo to give the title compound (145 mg) as a light yellow oil.

NMR ($d_6$-DMSO): δ (ppm) 7.71 (bd, 1H); 7.45 (dd, 1H); 7.38 (t, 1H); 7.03 (m, 2H); 4.86 (dd, 1H); 4.77 (d, 1H); 2.42 (dd, 1H); 2.31 (m, 4H).

MS (ES/+): m/z=206 [M+H]$^+$.

Intermediate 8

2-(R)-(4-Fluoro-2-methyl-phenyl)-piperidin-4-one

Palladium over charcoal (10%-74 mg) was added to a solution of intermediate 7 (145 mg) in MeOH (8 mL) and THF (2 mL). The mixture was allowed to react with hydrogen in a pressure reactor (2 atm) overnight. After flushing with Nitrogen, the solution was filtered and the solvent removed in vacuo. The crude product was purified by flash chromatography (AcOEt/MeOH 9:1) to give the title compound (26 mg) as a yellow oil.

The enantiomeric excess (90–95%) was detected by chiral HPLC.

T.l.c.: AcOEt/MeOH 9:1, Rf=0.2.
NMR ($d_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).

MS (ES/+): m/z=208 [MH]$^+$.
$[\alpha]_D$=+82.1 (c=1.07, DMSO).

Intermediate 9

2-(R)-(4-Fluoro-2-methyl-phenyl)-piperidin-4-one, L(+)-mandelate

A solution of L-(+)-mandelic acid (22.6 g) in AcOEt (308 mL) was added to a solution of intermediate 2 (31 g) in AcOEt (308 mL). Then isopropanol (616 mL) was added and the solution was concentrated in vacuo to 274 mL. The solution was then cooled to 0° C. and further cold isopropanol (96 mL) was added. The thick precipitate was stirred under Nitrogen for 5 hours at 0° C., then filtered and washed with cold Et$_2$O (250 mL) to give the title compound as a pale yellow solid (20.3 g).

M.p.: 82–85° C.
NMR ($d_6$-DMSO): δ (ppm) 7.51 (dd, 1H); 7.40 (m, 2H); 7.32 (m, 2H); 7.26 (m, 1H); 7.0 (m, 2H); 4.95 (s, 1H); 4.04 (dd, 1H); 3.31 (m, 1H); 2.88 (m, 1H); 2.49–2.2 (m, 4H); 2.29 (s, 3H). Chiral HPLC: HP 1100 HPLC system; column Chiralcel OD-H, 25 cm×4.6 mm; mobile phase: n-hexane/isopropanol 95:5+1% diethylamine; flow: 1.3 ml/min; detection: 240/215 nm; retention time 12.07 minutes.

Intermediate 10

2-(R)-4-Fluoro-2-methyl-phenyl-4-oxo-piperidine-1-carboxylic acid, (3,5-bis-trifluoromethyl-benzyl)-methylamide Method A
A solution of triphosgene (17 mg) in dry DCM (2 mL) was added to a solution of intermediate 8 (26 mg) and DIPEA (65 mg) in dry DCM (3 mL) previously cooled to 0°

C. under a Nitrogen atmosphere. After two hours acetonitrile (10 mL) was added, the temperature was allowed to reach r.t. and the DCM evaporated under a nitrogen flush. Then, a solution of 3,5-(bis-trifluoromethyl-benzyl)-methylamine hydrochloride (74 mg) and DIPEA (130 mg) in acetonitrile (3 mL) was added and the mixture was stirred at 23° C. overnight. The solvent was concentrated in vacua. The residue was dissolved in AcOEt (10 mL) and washed with 1N hydrochloric acid solution (3×5 mL), 5% sodium hydrogen carbonate (5 mL) and brine (10 mL). The organic layer was dried and concentrated in vacuo to a residue, which was purified by flash chromatography (CH/AcOEt 1:1) to give the title compound (50 mg) as a white solid.

Method B

A saturated sodium hydrogen carbonate solution (348 mL) was added to a solution of intermediate 9 (23.2 g) in AcOEt (348 mL) and the resulting mixture was vigorously stirred for 15 minutes. The aqueous layer was back-extracted with further AcOEt (230 mL) and the combined organic extracts were dried and concentrated in vacuo to give intermediate 8 (12.31 g) as a yellow oil, which was treated with TEA (20.5 mL) and AcOEt (123 mL). The solution obtained was added drop-wise over 40 minutes to a solution of triphosgene (8 g) in AcOEt (61 mL) previously cooled to 0° C. under a Nitrogen atmosphere, maintaining the temperature between 0° C. and 8° C.

After stirring for 2 hours at 20° C., 3,5-(bis-trifluoromethyl-benzyl)-methylamine hydrochloride (28.1 g), AcOEt (184 mL) and TEA (33 mL) were added to the reaction mixture which was then further stirred for 2 hours at 20° C.

The solution was washed with 10% sodium hydroxide solution (3×185 mL) and 1% hydrochloric acid solution (3×185 mL). The organic layer was dried and concentrated in vacuo to a crude (38 g), which was purified through a silica pad (CH/AcOEt from 9:1 to 1:1) to give the title compound (24.7 g) as a colourless oil.

NMR ($d_6$-DMSO): δ (ppm) 7.96 (s, 1H); 7.76 (s, 2H); 7.26 (dd, 1H); 6.98 (dd, 1H); 6.90 (td, 1H); 5.23 (t, 1H); 4.61 (d, 1H); 4.41 (d, 1H); 3.60 (m, 2H); 2.69 (m, 2H); 2.79 (s, 3H); 2.50 (m, 2H); 2.27 (s, 3H).

MS (ES/+): m/z=491 [MH]$^+$.

Intermediate 11

(E)-2-(R)-(4-Fluoro-2-methyl-phenyl)-4-hydroxy-imino-piperidine-1-carboxylic acid (3,5-bis-trifluoromethyl-benzyl)-methylamide (11a) and (Z)-2-(R)-(4-Fluoro-2-methyl-phenyl)-4-hydroxy-imino-piperidine-1-carboxylic acid, (3,5-bistrifluoromethyl-benzyl)-methylamide (11b)

Hydroxylamine hydrochloride (695 mg), sodium acetate (820.3 mg) and dry magnesium sulphate (500 mg) were added to a solution of intermediate 10 (500 mg) in dry MeOH (34 mL) under a Nitrogen atmosphere.

The mixture was stirred at r.t. overnight, then it was filtered over celite washing with DCM. The organic layer was washed with brine, dried and concentrated in vacuo to a residue which was purified by flash chromatography (CH/AcOEt 6:4) to give:
1. intermediate 11a (230 mg-white solid)
2. intermediate 11b (161 mg-white solid).

Intermediate 11a:

T.l.c.: AcOEt/Toluene 1:1, Rf=0.49.

$^1$H-NMR ($d_6$-DMSO): δ (ppm) 10.52 (s, 1H); 7.95 (bs, 1H); 7.71 (s, 2H); 7.37 (dd, 1H); 6.95 (dd, 1H); 6.88 (dt, 1H); 4.97 (dd, 1H); 4.47 (m, 2H); 3.59 (m, 1H); 3.49 (m, 1H); 2.77 (s, 3H); 2.53–2.67 (m, 4H); 2.30 (s, 3H).

MS (ES/+): m/z=506 [M+H]$^+$.

Intermediate 11b:

T.l.c.: AcOEt/Toluene 1:1, Rf=0.35.

$^1$H-NMR ($d_6$-DMSO): δ (ppm) 10.64 (s, 1H); 7.99 (bs, 1H); 7.84 (bs, 2H); 7.29 (dd, 1H); 6.91–7.00 (m, 2H); 5.00 (t, 1H); 4.64 (d, 1H); 4.43 (d, 1H); 3.12–3.35 (m, 2H); 2.72–2.88 (m, 5H); 2.2–2.5 (m, 5H).

MS (ES/+): m/z=506 [M+H]$^+$.

Intermediate 12

2-(S)-(4-Fluoro-2-methyl-phenyl)-5-oxo-[1,4]-diazepane-1-carboxylic acid, (3,5-bis-trifluoromethyl-benzyl)-methylamide A solution of p-tosyl chloride (111 mg) in acetone (1.9 mL) was added dropwise to a mixture of intermediate 11a (196 mg) in acetone (3.9 mL) and 5% sodium carbonate solution (3.9 mL) under a Nitrogen atmosphere. The mixture was stirred overnight at room temperature, then concentrated in vacuo to eliminate the acetone and the aqueous residue was extracted with DCM. The organic layer was washed with brine, dried and concentrated in vacuo to a residue which was purified by flash chromatography (from CH/AcOEt 6:4 to AcOEt) to give the title compound (55 mg) as a colourless oil.

$^1$H-NMR ($d_6$-DMSO): δ (ppm) 7.73 (s, 1H); 7.45 (s, 2H); 7.21 (dd, 1H) 6.78–6.88 (m, 2H); 5.74 (dd, 1H); 4.87 (dd, 1H); 4.53 (d, 1H); 4.31 (d, 1H); 3.55 (t, 2H); 3.40–3.55 (m, 2H); 2.89 (m, 2H); 2.85 (s, 3H); 2.33 (s, 3H).

MS (ES/+): m/z=506 [M+H]$^+$.

Intermediate 13

7-(R)-(4-Fluoro-2-methyl-phenyl)-5-oxo-[1,4]-diazepane-1-carboxylic acid (3,5-bis-trifluoromethyl-benzyl)-methylamide A solution of p-tosyl chloride (91.17 mg) in acetone (1.6 mL) was added drop-wise to a mixture of intermediate 11b (161 mg) in acetone (3.2 mL) and 5% sodium carbonate solution (3.2 mL) under a Nitrogen atmosphere. The mixture was stirred for 15 minutes at room temperature then it was heated to reflux for 45 minutes.

The mixture was concentrated in vacuo to eliminate the acetone and the aqueous residue was extracted with DCM (3×20 mL). The organic layer was dried and concentrated in vacuo to a residue which was purified by flash chromatography (AcOEt) to give the title compound (135 mg) as a colourless oil.

$^1$H-NMR ($d_6$-DMSO): δ (ppm) 7.79 (bs, 1H); 7.57 (bs, 2H); 7.37 (dd, 1H); 6.86 (m, 2H); 5.87 (bt, 1H); 5.08 (dd, 1H); 4.47 (m, 2H); 3.45–3.70 (m, 4H); 3.11 (dd, 1H); 2.97 (dd, 1H); 2.81 (s, 3H); 2.32 (s, 3H).

MS (ES/+): m/z=506 [M+H]$^+$.

Intermediates 14

(E)-2-(R)-(4-Fluoro-2-methyl-phenyl)-4-hydroxy-imino-piperidine-1-carboxylic acid, [1-(R)-(3,5-bis-trifluoromethyl-phenyl)-ethyl]-methylamide (14a) and (Z)-2-(R)-(4-Fluoro-2-methyl-phenyl)-4-hydroxy-imino-piperidine-1-carboxylic acid, [1-(R)-(3,5-bis-trifluoromethyl-phenyl)-ethyl]-methylamide (14b)

Hydroxylamine hydrochloride (645 mg), sodium acetate (765 mg) and dry magnesium sulphate (500 mg) were added to a solution of intermediate 4a (532 mg) in dry MeOH (30 mL) under a Nitrogen atmosphere.

The mixture was stirred at r.t. overnight, then it was filtered over celite washing with DCM. The organic layer was washed with brine, dried and concentrated in vacuo to a residue which was purified by flash chromatography (CH/AcOEt 6:4) to give the title compounds in two fractions:
1. intermediate 14a (220 mg-white solid)
2. intermediate 14b (154 mg-white solid)

Intermediate 14a:
T.l.c.: CH/AcOEt 1:1, Rf=0.6.
$^1$H-NMR ($d_6$-DMSO): δ (ppm) 10.51 (s, 1H); 7.96 (bs, 1H); 7.71 (bs, 2H); 7.35 (dd, 1H); 6.94 (dd, 1H); 6.84 (dt, 1H); 5.03 (m, 2H); 3.59 (m, 2H); 2.4–2.68 (m, 7H); 2.30 (s, 3H); 1.54 (d, 3H).
MS (ES/+): m/z=520 [M+H]$^+$.

Intermediate 14b:
T.l.c. CH/AcOEt 1:1, Rf=0.5.
$^1$H-NMR ($d_6$-DMSO): δ (ppm) 10.63 (s, 1H); 8.00 (bs, 1H); 7.84 (bs, 2H); 7.27 (dd, 1H); 6.99 (dd, 1H); 6.89 (dt, 1H); 5.16 (q, 1H); 5.02 (t, 1H); 3.36 (m, 1H); 3.09 (m, 1H); 2.93 (dd, 1H); 2.68 (dd, 1H); 2.58 (s, 3H); 2.21–2.34 (m, 5H); 1.58 (d, 3H).
MS (ES/+): m/z=520 [M+H]$^+$.

Intermediate 15

2-(R)-4-Fluoro-2-methyl-phenyl)-4-oxo-piperidine-1-carboxylic acid, (3,5-dichloro-benzyl)-methylamide A saturated sodium hydrogen carbonate solution (20 mL) was added to a solution of intermediate 9 (1.0 g) in AcOEt (30 mL) and the resulting mixture was vigorously stirred for 15 minutes. The aqueous layer was back-extracted with further AcOEt (30 mL) and the combined organic extracts were dried and concentrated in vacuo to give intermediate 8 (0.55 g) as a yellow oil, which was treated with TEA (0.92 mL) and AcOEt (5.5 mL). The solution obtained was added drop-wise over 40 minutes to a solution of triphosgene (0.385 g) in AcOEt (2.5 mL) previously cooled to 0° C. under a Nitrogen atmosphere, maintaining the temperature between 0° C. and 8° C.

After stirring for 2 hours at 20° C., 3,5-(dichloro-benzyl)-methylamine hydrochloride (0.72 g), AcOEt (8.25 mL) and TEA (1.84 mL) were added to the reaction mixture which was then further stirred for 2 hours at 20° C.

The solution was washed with a 20% sodium hydroxide solution (20 mL). The organic layer was dried and concentrated in vacuo to a crude (1.24 g), which was purified through a silica pad (CH/AcOEt from 9:1 to 1:1) to give the title compound (0.87 g) as a colourless oil.

NMR ($d_6$-DMSO): δ (ppm) 7.45 (t, 1H); 7.29 (m, 1H); 7.07 (d, 2H); 7.0–6.94 (m, 2H); 5.16 (dd, 1H); 4.4–4.26 (dd, 2H); 3.35 (m, 2H); 2.76 (s, 3H); 2.75–2.6 (m, 2H); 2.5 (m, 2H); 2.29 (s, 3H).

Intermediate 16

(E)-2-(R)-(4-Fluoro-2-methyl-phenyl)-4-hydroxy-imino-piperidine-1-carboxylic acid, (3,5-dichloro-benzyl)-methylamide (16a) (and (Z)-2-(R)-(4-Fluoro-2-methyl-phenyl)-4-hydroxy-imino-piperidine-1-carboxylic acid, (3,5-dichloro-benzyl)-methylamide (16b)

Hydroxylamine hydrochloride (799 mg), sodium acetate (943 mg) and dry magnesium sulphate (500 mg) were added to a solution of intermediate 15 (486 mg) in dry MeOH (38 mL) under a nitrogen atmosphere.

The mixture was stirred at r.t. overnight, then it was filtered over celite washing with AcOEt. The organic layer was washed with brine, dried and concentrated in vacuo to a residue which was purified by flash chromatography (CH/AcOEt 6:4) to give:
1. intermediate 16a (173 mg-white solid)
2. intermediate 16b (152 mg-white solid).

Intermediate 16a:
T.l.c.: CH/AcOEt 1:1, Rf=0.38.
$^1$H-NMR ($d_6$-DMSO): δ (ppm) 10.49 (s, 1H); 7.43 (t, 1H); 7.35 (dd, 1H); 7.00 (s, 2H); 6.94 (m, 2H); 4.9 (t, 1H); 4.27 (m, 2H); 3.58 (m, 1H); 3.42 (m, 1H); 2.71 (s, 3H); 2.64–2.4 (m, 4H); 2.3 (s, 3H).
MS (ES/+): m/z=438 [M+H]$^+$.

Intermediate 16b:
T.l.c.: CH/AcOEt 1:1, Rf=0.24.
$^1$H-NMR ($d_6$-DMSO): δ (ppm) 10.64 (s, 1H); 7.46 (t, 1H); 7.29 (m, 1H); 7.12 (d, 2H); 7.05–6.9 (m, 2H); 4.87 (t, 1H); 4.42–4.25 (dd, 2H); 3.4–3.1 (m, 2H); 2.75–2.7 (s+m, 3H); 2.36 (m, 2H); 2.24 (s, 3H).
MS (ES/+): m/z=438 [M+H]$^+$.

Intermediate 17

2-(S)-(4-Fluoro-2-methyl-phenyl)-5-oxo-[1,4]-diazepane-1-carboxylic acid, (3,5-dichloro-benzyl)-methylamide A solution of p-tosyl chloride (111.5 mg) in acetone (1.9 mL) was added drop-wise to a mixture of intermediate 16a (173 mg) in acetone (4 mL) and 5% sodium carbonate solution (4 mL) under a Nitrogen atmosphere. The mixture was stirred at r.t. for 2 hours, then it was heated to reflux for 1.15 hour. The mixture was concentrated in vacuo to eliminate the acetone and the aqueous residue was extracted with DCM. The organic layer was washed with brine, dried and concentrated in vacuo to a residue which was purified by flash chromatography (from AcOEt to AcOEt/MeOH 95:5) to give the title compound (195 mg) as a colourless oil.

T.l.c.: AcOEt, Rf=0.1.
$^1$H-NMR ($d_6$-DMSO): δ (ppm) 7.23 (s, 1H); 6.89 (m, 2H); 6.84 (s, 2H); 5.85 (bt, 1H); 4.85 (t, 1H); 4.43–4.19 (d, 2H); 3.56 (m, 2H); 3.5 (t, 2H); 2.91 (m, 3H); 2.87 (s, 3H); 2.38 (s, 3H).
MS (ES/+): m/z=438 [M+H]$^+$.

Intermediate 18

7-(R)-(4-Fluoro-2-methyl-phenyl)-5-oxo-[1,4]-diazepane-1-carboxylic acid (3,5-dichloro-benzyl)-methylamide A solution of p-tosyl chloride (99.5 mg) in acetone (1.7 mL) was added drop-wise to a mixture of intermediate 16b (152 mg) in acetone (3.5 mL) and 5% sodium carbonate solution (3.5 mL) under a Nitrogen atmosphere. The mixture was stirred at room temperature for 2 hours, then it was heated to reflux for 1.5 hour.

The mixture was concentrated in vacuo to eliminate the acetone and the aqueous residue was extracted with DCM (2×20 mL). The organic layer was dried and concentrated in vacuo to a residue which was purified by flash chromatography (from AcOEt to AcOEt/MeOH 9:1) to give the title compound (102 mg) as a colourless oil.

T.l.c.: AcOEt, Rf=0.05.

$^1$H-NMR (d$_6$-DMSO): δ (ppm) 7.35 (dd, 1H); 7.24 (s, 1H); 6.89 (s, 2H); 6.86 (m, 2H); 6.01 (bs, 1H); 5.01 (dd, 1H); 4.35–4.25 (d, 2H); 3.6–3.4 (m, 4H); 3.13 (dd, 1H); 2.9 (dd, 1H); 2.79 (s, 3H); 2.33 (s, 3H).

MS (ES/+): m/z=438 [M+H]$^+$.

Intermediate 19

(E)-2-(R)-(4-Fluoro-2-methyl-phenyl)-4-hydroxyimino-piperidine-1-carboxylic acid, [1-(S)-(3,5-bis-trifluoromethyl-phenyl)-ethyl]-methylamide (19a)
and (Z)-2-(R)-(4-Fluoro-2-methyl-phenyl)-4-hydroxyimino-piperidine-1-carboxylic acid, [1-(S)-(3,5-bis-trifluoromethyl-phenyl)-ethyl]-methylamide (19b)

Hydroxylamine hydrochloride (695 mg), sodium acetate (820 mg) and dry magnesium sulphate (500 mg) were added to a solution of intermediate 5b (500 mg) in dry MeOH (50 mL) under a Nitrogen atmosphere.

The mixture was stirred at r.t. 6 hours, then it was filtered over celite washing with DCM. The organic layer was washed with brine, dried and concentrated in vacuo to a residue which was purified by flash chromatography (CH/AcOEt 6:4) to give:
1. intermediate 19a (200 mg-white solid)
2. intermediate 19b (130 mg-white solid).

Intermediate 19a:

$^1$H-NMR (d$_6$-DMSO): δ (ppm) 10.51 (s, 1H); 7.94 (bs, 1H); 7.7 (bs, 2H); 2H); 7.36 (dd, 1H); 6.95 (dd, 1H); 6.89 (dt, 1H); 5.21 (q, 1H); 4.95 (dd, 1H); 3.51 (m, 1H); 3.41 (m, 1H); 2.69 (m, 2H); 2.6–2.4 (m, 2H); 2.69 (s, 3H); 2.29 (s, 3H); 1.5 (d, 3H).

Intermediate 19b:

$^1$H-NMR (d$_6$-DMSO): δ (ppm) 10.64 (s, 1H); 7.99 (bs, 1H); 7.82 (bs, 2H); 7.28 (dd, 1H); 7.0 (dd, 1H); 6.9 (dt 1H); 5.33 (q, 1H); 5.01 (t, 1H); 3.35 (m, 1H); 3.07 (m, 1H); 2.9 (dd, 1H); 2.7 (dd, 2H); 2.67 (s, 2H); 2.33 (m, 2H); 2.22 (s, 3H); 1.56 (d, 3H).

Intermediate 20

2-(S)-(4-Fluoro-2-methyl-phenyl)-5-oxo-[1,4]-diazepane-1-carboxylic acid, [1-(S)-(3,5-bis-trifluoromethyl-phenyl)-ethyl]-methylamide A solution of p-tosyl chloride (110.2 mg) in acetone (1.9 mL) was added drop-wise to a mixture of intermediate 19a (196 mg) in acetone (3.9 mL) and 5% sodium carbonate solution (4 mL) under a Nitrogen atmosphere. The mixture was stirred at room temperature for 15 minutes, then it was heated to reflux for 45 minutes. The mixture was allowed to cool to r.t., concentrated in vacuo to eliminate the acetone and the aqueous residue was extracted with DCM. The organic layer was washed with a 5% sodium hydrogen carbonate solution (10 mL). The aqueous phase was re-extracted with DCM (3×20 mL). The combined organic extracts were dried and concentrated in vacuo to a residue which was purified by flash chromatography (from AcOEt to AcOEt/MeOH 9:1) to give the title compound (110 mg) as a white solid.

T.l.c.: AcOEt 100%, Rf=0.35.

IR (nujol, cm$^{-1}$): 3240 (NH), 1662 (C=O).

$^1$H-NMR (d$_6$-DMSO): δ (ppm) 7.93 (s, 1H); 7.64 (s, 2H); 7.48 (t, 1H) 7.22 (dd, 1H); 6.97 (dd, 1H); 6.83 (dt, 1H); 5.16 (q, 1H); 4.68 (t, 1H); 3.51 (m, 1H); 3.42 (m, 1H);3.3 (m, 2H); 2.8 (m, 1H); 2.62 (m, 1H); 2.68 (s, 3H); 2.3 (s, 3H); 1.48 (d, 3H).

MS (ES/+): m/z=520 [M+H]$^+$.

Intermediate 21

7-(R)-(4-Fluoro-2-methyl-phenyl)-5-oxo-[1,4]-diazepane-1-carboxylic acid, [1-(S)-(3,5-bis-trifluoromethyl-phenyl-ethyl]-methylamide A solution of p-tosyl chloride (72 mg) in acetone (1.2 mL) was added drop-wise to a mixture of intermediate 19b (130 mg) in acetone (2.5 mL) and 5% sodium carbonate solution (2.5 mL) under a Nitrogen atmosphere. The mixture was stirred at room temperature for 15 minutes, then it was heated to reflux for 45 minutes. The mixture was allowed to cool to r.t., concentrated in vacuo to eliminate the acetone and the aqueous residue was extracted with DCM. The organic layer was washed with a 5% sodium hydrogen carbonate solution (10 mL). The aqueous phase was re-extracted with DCM (3×20 mL). The combined organic extracts were dried and concentrated in vacuo to a residue which was purified by flash chromatography (from CH/AcOEt 1:1 to AcOEt 100%) to give the title compound (82 mg) as a white solid.

T.l.c.: AcOEt 100%, Rf=0.33.

$^1$H-NMR (d$_6$-DMSO): δ (ppm) 7.95 (s, 1H); 7.37 (dd, 1H) 7.0 (bs, 1H); 6.96 (dd, 1H); 6.86 (dt, 1H); 5.23 (q, 1H); 4.68 (dd, 1H); 3.5–3.15 (m, 4H); 2.96 (dd, 1H); 2.65 (s, 3H); 2.5 (m, 1H); 2.24 (s, 3H); 1.5 (d, 3H).

MS (ES/+): m/z=520 [M+H]$^+$.

Intermediate 22

2-(R)-4-Fluoro-2-methyl-phenyl)-4-oxo-piperidine-1-carboxylic acid, (3-chloro-4-fluoro-benzyl)-methylamide A solution of triphosgene (120 mg) in anhydrous DCM (5 mL) was dropped over 40 minutes into a solution of intermediate 8 (0.5 g) and TEA (0.6 mL) in anhydrous DCM (5 mL) previously cooled to 0° C. under a Nitrogen atmosphere. After stirring for 2 hours at r.t., a solution of (3-chloro-4-fluoro-benzyl)-methylamine hydrochloride (0.72 g) and DIPEA (0.42 mL) in anhydrous DCM (5 mL) were added and the reaction mixture was stirred at r.t. overnight. The solution was washed with 1N hydrochloric acid solution (3×5 mL), 5% sodium hydrogen carbonate (5 mL) and brine (10 mL). The organic layer was dried and concentrated in vacuo to give the title compound (0.4 g), which was used for the next reaction without any further purification.

¹H-NMR (d₆-DMSO): δ (ppm) 7.31 (m, 1H); 7.27 (d, 1H) 7.2 (dd, 1H); 7.15 (m, 1H); 6.98 (m, 2H); 5.17 (t, 1H); 4.31 (s, 2H); 3.53 (t, 2H); 2.73 (s, 3H); 2.7 (m, 2H);2.5 (m, 2H); 2.28 (s, 3H).

Intermediate 23

(E)-2-(R)-(4-Fluoro-2-methyl-phenyl)-4-hydroxy-imino-piperidine-1-carboxylic acid, (3-chloro-4-fluoro-benzyl)-methylamide (23a) and (Z)-2-(R)-(4-Fluoro-2-methyl-phenyl)-4-hydroxy-imino-piperidine-1-carboxylic acid, (3-chloro-4-fluoro-benzyl)-methylamide (23b)

Hydroxylamine hydrochloride (695 mg) was added to a mixture of intermediate 22 (400 mg) sodium acetate (820 mg) and dry magnesium sulphate (500 mg) in dry MeOH (30 mL) under a Nitrogen atmosphere.

The mixture was stirred at r.t. overnight, then it was filtered over celite washing with DCM. The organic layer was washed with brine. The aqueous layer was re-extracted with DCM (3×20 mL). The combined organic extracts were dried and concentrated in vacuo to a residue which was purified by flash chromatography (CH/AcOEt 1:1) to give:
1. intermediate 23a (160 mg-white solid)
2. intermediate 23b (110 mg-white solid).

Intermediate 23a:
T.l.c.: Toluene/AcOEt 1:1, Rf=0.42.
¹H-NMR (d₆-DMSO): δ (ppm) 10.5 (s, 1H); 7.37 (t, 1H); 7.3 (dd, 1H); 7.12 (s, 2H); 7.09 (m, 1H); 6.97–6.9 (m, 2H); 4.92 (dd, 1H); 4.25 (m, 2H); 3.55 (m, 1H); 3.42 (m, 1H); 2.69 (s, 3H); 2.65–2.5 (m, 4H); 2.3 (s, 3H).
MS (ES/+): m/z=422 [M+H]⁺.

Intermediate 23b:
T.l.c.: Toluene/AcOEt 1:1, Rf=0.25.
¹H-NMR (d₆-DMSO): δ (ppm) 10.6 (s, 1H); 7.32 (m, 1H); 7.29 (dd, 1H); 7.28–7.1 (m, 2H); 7.0–6.9 (m, 2H); 4.9 (t, 1H); 4.4–4.25 (m, 2H); 3.3 (m, 1H); 3.12 (m, 1H); 2.77 (d, 2H); 2.72 (s, 3H;); 2.4–2.25 (m, 2H); 2.24 (s, 3H).
MS (ES/+): m/z=422 [M+H]⁺.

Intermediate 24

2-(R)-4-Fluoro-2-methyl-phenyl)-4-oxo-piperidine-1-carboxylic acid, (2,5-dichloro-benzyl)-methylamide A solution of triphosgene (108 mg) in anhydrous DCM (2 mL) was added drop-wise to a solution of intermediate 8 (152 mg) and TEA (0.41 mL) in anhydrous DCM (5 mL) previously cooled to 0° C. under a Nitrogen atmosphere.

After stirring for 1 hours at 0° C., a solution of 2,5-(dichloro-benzyl)-methylamine hydrochloride (249 mg) and DIPEA (0.5 mL) in anhydrous DCM (3 mL) was added to the reaction mixture, which was stirred at r.t. overnight.

The solution was diluted with AcOEt (50 mL), washed with a 1M hydrochloric acid solution (3×10 mL) and brine (3×10 mL). The organic layer was dried and concentrated in vacuo to a residue, which was purified by flash chromatography (CH/AcOEt from 8:2) to give the title compound (248 mg) as a colourless oil.

NMR (d₆-DMSO): δ (ppm) 7.46 (d, 1H); 7.35 (dd, 1H); 7.3 (m, 1H); 7.0 (d, 1H); 6.94 (m, 2H); 5.19 (dd, 1H); 4.47 (d, 2H); 4.25 (d, 1H); 3.56 (t, 2H); 2.7–2.5 (m, 2H); 2.82 (s, 3H); 2.8–2.6 (m, 2H); 2.28 (s, 3H).
MS (ES/+): m/z=423 [M+H]⁺.

Intermediate 25

(E)-2-(R)-(4-Fluoro-2-methyl-phenyl)-4-hydroxy-imino-piperidine-1-carboxylic acid, (2,5-dichloro-benzyl)-methylamide (25a) and (Z)-2-(R)-(4-Fluoro-2-methyl-phenyl)-4-hydroxy-imino-piperidine-1-carboxylic acid, (2,5-dichloro-benzyl)-methylamide (25b)

Hydroxylamine hydrochloride (410 mg), sodium acetate (484 mg) and dry magnesium sulphate (500 mg) were added to a solution of intermediate 24 (19 mg) in dry MeOH (38 mL) under a Nitrogen atmosphere.

The mixture was stirred at r.t. overnight, then it was filtered over celite washing with AcOEt. The organic layer was washed with brine, dried and concentrated in vacuo to a residue which was purified by flash chromatography (CH/AcOEt 6:4) to give:
1. intermediate 25a (86 mg-white solid)
2. intermediate 25b (43 mg-white solid).

Intermediate 25a:
T.l.c.: CH/AcOEt 1:1, Rf=0.5.
¹H-NMR (CDCl₃): δ (ppm) 7.35–7.26 (m, 2H); 7.18 (dd, 1H); 6.98 (d, 1H); 6.9–6.84 (m, 2H); 5.14 (dd, 1H); 4.58 (d, 1H); 4.28 (d, 1H); 3.6–3.4 (m, 2H); 2.86 (s, 3H); 2.8–2.55 (m, 4H); 2.36 (s, 3H).
MS (ES/+): m/z=438 [M+H]⁺.

Intermediate 25b:
T.l.c.: CH/AcOEt 1:1, R=0.4.
¹H-NMR (CDCl₃): δ (ppm) 7.35–7.26 (m, 2H); 7.22 (dd, 1H); 7.11 (d, 1H); 6.95–6.85 (m, 2H); 5.22 (t, 1H); 4.66 (d, 1H); 4.36 (d, 1H); 3.45–3.2 (m, 2H); 3.15–3.0 (dd, 2H); 2.88 (s, 3H); 2.45 (m, 2H); 2.35 (s, 3H).
MS (ES/+): m/z=438 [M+H]⁺.

Intermediate 26

1-(Benzyloxycarbonyl)-2-(4-fluoro-phenyl)-2,3-dihydro-4-pyridone

A solution of benzyl chloroformate (48.7 mL) in dry THF (60 mL) was added to a solution of 4-methoxypyridine (25 mL) in dry THF (900 mL) previously cooled at −23° C. under a Nitrogen atmosphere.

The mixture was stirred at −23° C. for 50 minutes, then p-fluorophenyl magnesium bromide (1M in THF-48.7 mL) was added. The solution was stirred at −20° C. for 1 hour, then it was warmed up to 20° C. and a 10% hydrochloric acid solution (560 mL) was added. The aqueous layer was extracted with AcOEt (1000 mL).

The organic extract was washed with 5% sodium hydrogen carbonate solution (600 mL) and brine (600 mL) then partially concentrated in vacuo.

CH (200 mL) was added dropwise over 1 hour at 20° C. and the resulting mixture was stirred at r.t. for 10 minutes, then at 0° C. for 1.5 hours. The solid obtained was filtered off to give the title compound as a white solid (51.6 g).

NMR (d₆-DMSO): δ (ppm) 8.05 (d, 1H); 7.4–7.3 (m, 5H); 7.24 (dd, 2H); 7.15 (t, 1H); 5.73 (d, 1H); 5.29 (d, 1H); 5.24 (dd, 2H); 3.25 (dd, 1H); 2.62 (d, 1H); 2.26 (s, 3H).
MS (EI/+): m/z=325 [M]⁺.

Intermediate 27

1-Benzyloxycarbonyl 2-(4-fluoro-phenyl)-piperidine-4-one

L-selectride (1M solution in THF, 62 mL) was added drop-wise, over 80 minutes, to a solution of intermediate 26 (20 g) in dry THF (300 mL) previously cooled to −72° C. under a Nitrogen atmosphere. After 45 minutes, the solution was allowed to warm to −30° C. and 2% sodium hydrogen carbonate solution (280 mL) was added drop-wise. The solution was extracted with AcOEt (3×280 mL). The combined organic phases were washed with water (80 mL) and brine (160 mL). The organic phase was dried and concentrated in vacuo to give the title compound as a pale yellow oil (27 g).

NMR ($d_6$-DMSO): δ (ppm) 7.26 (m, 7H); 7.17 (t, 2H); 5.53 (bt, 1H); 5.12 (m, 2H); 4.1 (m, 1H); 3.44 (m, 1H); 3.01–2.84 (2dd, 2H); 2.54–2.3 (m, 2H).

Intermediate 28

2-(4-Fluoro-phenyl)-piperidine-4-one

Intermediate 27 (94 g) was dissolved in AcOEt (300 mL), then 10% Pd/C (6.8 g) was added under a Nitrogen atmosphere. The slurry was hydrogenated at 1 atmosphere for 3 hours. The mixture was filtered through Celite and the organic phase was concentrated in vacuo to give the crude 2-(4-fluoro-phenyl)-piperidine-4-one (10 g).

A part of this material (9 g) was purified by flash chromatography (from CH/AcOEt 7:3 to AcOEt 100%) to give the title compound as a yellow oil (5 g).

NMR ($d_6$-DMSO): δ (ppm) 7.43 (m, 2H); 7.15 (m, 2H); 3.86 (dd, 1H); 3.29 (m, 1H); 2.87 (bs, 1H); 2.81 (m, 1H); 2.48 (m, 1H); 2.42 (m, 1H); 2.33 (m, 1H); 2.19 (m, 1H).

Intermediate 29

2-(R)-(4-Fluoro-phenyl)-piperidine-4-one, (+)-O,O'-dibenzoyl-D-tartrate

A solution of intermediate 28 (1 g) in isopropanol (10 mL) was added to (+)-O,O'-dibenzoyl-D-tartaric acid acid (1.86 g) and the solution was heated to 50° C. for 30 minutes, then it was cooled to 0° C. and left at this temperature overnight. The solid was filtered off to give the title compound as a white solid (270 mg).

NMR ($d_6$-DMSO): δ (ppm) 12.3 (bs, 2H); 7.67 (t, 2H); 7.54 (t, 4H); 7.49 (dd, 2H); 7.18 (t, 2H); 5.96 (d, 4H); 5.75 (s, 2H); 4.28 (bd, 1H); 3.41 (dd, 1H); 3.09 (dt, 1H); 2.72 (t, 1H); 2.64 (m, 1H); 2.42 (dd, 1H); 2.3 (m, 1H).

Chiral HPLC: HP 1100 HPLC system; column Chiralcel OD-H, 25 cm×4.6 mm×5; mobile phase: n-hexane/isopropanol 95:5+1% diethylamine; flow: 1.3 ml/min; detection: 254 nm; retention time 17.85 minutes; e.e. 93%.

Intermediate 30

2-(R)-(4-Fluoro-phenyl)-4-oxo-piperidine-1-carboxylic acid, (3,5-bis-trifluoromethyl-benzyl)-methylamide A saturated sodium hydrogen carbonate solution (30 mL) was added to a solution of intermediate 29 (630 mg) in AcOEt (30 mL) and the resulting mixture was vigorously stirred for 15 minutes. The aqueous layer was back-extracted with further AcOEt (30 mL) and the combined organic extracts were dried and concentrated in vacuo to give 2-(R)-(4-fluoro-phenyl)-piperidine-4-one (214 mg).

A solution of triphosgene (165 mg) in anhydrous DCM (3.5 mL) was added drop-wise to a solution of this intermediate (214 mg) and TEA (0.6 mL) in anhydrous DCM (7.5 mL) previously cooled to 0° C. under a Nitrogen atmosphere.

After stirring for 2.5 hours at 0° C., a solution of 3,5-(bis-trifluoromethyl-benzyl)-methylamine hydrochloride (422.6 mg) and TEA (0.9 mL) in anhydrous DCM (8 mL) was added to the reaction mixture, which was stirred at r.t. for 4 hours.

The solution was diluted with AcOEt (50 mL), washed with a 1M hydrochloric acid solution (3×20 mL) and brine (3×20 mL). The organic layer was dried and concentrated in vacuo to a residue, which was purified by flash chromatography (CH/AcOEt 7:3) to give the title compound (370 mg) as a colourless oil.

NMR (CDCl$_3$): δ (ppm) 7.82 (s, 1H); 7.71 (s, 2H); 7.28 (m, 2H); 7.03 (t, 2H); 5.39 (t, 1H); 4.57 (2d, 2H); 3.73 (m, 1H); 3.29 (m, 1H); 2.98 (m, 2H); 2.94 (s, 3H); 2.59 (m, 1H); 2.42 (m, 1H).

MS (ES/+): m/z=477 [M+H]$^+$.

EXAMPLE 1

2-(S)-(4-Fluoro-2-methyl-phenyl)-[1,4]-diazepane-1-carboxylic acid, (3,5-bis-trifluoromethyl-benzyl)-methylamide hydrochloride Borane (1 M solution in THF-0.6 mL) was added drop-wise to a solution of intermediate 12 (101 mg) in anhydrous THF (5.3 mL) under a Nitrogen atmosphere.

The mixture was heated to reflux for 1.5 hour. Then, the solution was cooled to 0° C. and a 6M hydrochloric acid solution (5 mL) was added. The mixture was allowed to warm to r.t. and stirred for 4 hours. After concentration in vacuo to eliminate the THF, the aqueous solution was cooled to 0° C. and treated with solid sodium hydroxide until pH=9. The mixture was extracted with DCM (4×15 mL). The combined organic extracts were dried and concentrated in vacuo to a residue which was purified by chromatography (from AcOEt/MeOH 8:2 to 7:3) to give 2-(S)-(4-fluoro-2-methyl-phenyl)-[1,4]-diazepane-1-carboxylic acid, (3,5-bis-trifluoromethyl-benzyl)-methylamide (40 mg).

This material was dissolved in dry Et$_2$O (1 mL) and treated with hydrochloric acid (1M in Et$_2$O-0.3 mL) at 0° C. The resulting solution was stirred at r.t. for 15 minutes, then pentane (3 mL) was added and decanted twice. The residue was dried in vacuo to give the title compound (34 mg) as a white foam.

$^1$H-NMR (d$_6$-DMSO): δ (ppm) 9.38 (bs, 1H); 9.12 (bm, 1H); 7.93 (bs, 1H); 7.66 (bs, 2H); 7.34 (dd, 1H); 6.97–6.91 (m, 2H); 5.38 (dd, 1H); 4.38 (m, 2H); 3.91–3.6 (m, 3H); 3.33–3.23 (m, 2H); 2.96 (m, 1H): 2.66 (s, 3H); 2.36 (s, 3H); 2.05–1.86 (m, 2H).

MS (ES/+): m/z=492 [M+H−H-HCl]$^+$.

EXAMPLE 2

7-(R)-(4-Fluoro-2-methyl-phenyl)-[1,4]-diazepane-1-carboxylic acid, (3,5-bis-trifluoromethyl-benzyl)-methylamide hydrochloride Borane (1 M solution in THF-0.8 mL) was added drop-wise to a solution of intermediate 13 (135 mg) in anhydrous THF (8 mL) under a Nitrogen atmosphere.

The mixture was heated to reflux for 1.5 hours. Then, the solution was cooled to 0° C. and a 6M hydrochloric acid solution (8 mL) was added. The mixture was allowed to warm to r.t. and stirred for 4 hours. After concentration in vacuo to eliminate the THF, the aqueous residue was cooled to 0° C. and treated with solid sodium hydroxide until pH=9. The mixture was extracted with DCM (4×15 mL). The combined organic extracts were dried and concentrated in vacuo to a residue which was purified by flash chromatography (from AcOEt/MeOH 7:3 to 6:4) to give 7-(R)-(4-fluoro-2-methyl-phenyl)-[1,4]-diazepane-1-carboxylic acid, (3,5-bis-trifluoromethyl-benzyl)-methylamide (50 mg).

This material was dissolved in dry Et$_2$O (1 mL) and treated with hydrochloric acid (1M in Et$_2$O-0.4 mL) at 0° C. The resulting solution was stirred at r.t. for 15 minutes, then pentane (3 mL) was added and decanted twice. The residue was dried in vacuo to give the title compound (34 mg) as a white foam.

$^1$H-NMR (d$_6$-DMSO): δ (ppm) 8.98 (bs, 2H); 7.95 (bs, 1H); 7.71 (bs, 2H); 7.32 (dd, 1H); 6.91 (m, 2H); 5.13 (dd, 1H); 4.38 (m, 2H); 3.96 (dd, 1H); 3.73 (dd, 1H); 3.39–3.15 (m, 4H); 2.68 (s, 3H); 2.26–2.12 (m, 5H).

MS (ES/+): m/z=492 [M+H−HCl]$^+$.

EXAMPLE 3

2-(S)-(4-Fluoro-2-methyl-phenyl)-[1,4]-diazepane-1-carboxylic acid, [1-(R)-(3,5-bis-trifluoromethyl-phenyl)-ethyl]-methylamide hydrochloride A solution of p-tosyl chloride (123 mg) in acetone (2 mL) was added drop-wise to a mixture of intermediate 14a (220 mg) in acetone (4.3 mL) and 5% sodium carbonate solution (4.3 mL) under a Nitrogen atmosphere. The mixture was stirred for 30 min. at room temperature then it was heated to reflux for 1 hour.

The mixture was concentrated in vacuo to eliminate the acetone and the aqueous residue was extracted twice with DCM. The organic layer was dried and concentrated in vacuo to a residue which was purified by chromatography (AcOEt 100%) to give 2-(S)-(4-fluoro-2-methyl-phenyl)-5-oxo-[1,4]-diazepane-1-carboxylic acid, [1-(R)-(3,5-bis-trifluoromethyl-phenyl)-ethyl]-methylamide (150 mg) as a colourless oil.

Borane (1 M solution in THF-0.8 mL) was added drop-wise to a solution of this intermediate (145 mg) in anhydrous TBF (8 mL) under a nitrogen atmosphere.

The mixture was heated to reflux for 2 hours. Then, the solution was cooled to 0° C. and a 6M hydrochloric acid solution (8 mL) was added. The mixture was allowed to warm to r.t. and stirred overnight. After concentration in vacuo to eliminate the THF, the aqueous solution was cooled to 0° C. and treated with solid sodium hydroxide until pH=9. The mixture was extracted with DCM (4×20 mL). The combined organic extracts were dried and concentrated in vacuo to a residue which was purified by chromatography (from AcOEt to AcOEt/MeOH 95:5) to give 2-(S)-4-fluoro-2-methyl-phenyl)-[1,4]-diazepane-1-carboxylic acid, [1-(R)-(3,5-bis-trifluoromethyl-phenyl)-ethyl]-methylamide (68 mg).

This material was dissolved in dry Et$_2$O (1.6 mL) and treated with hydrochloric acid (1M in Et$_2$O-0.5 mL) at 0° C. The resulting solution was stirred at r.t. for 15 minutes, then pentane (3 mL) was added and decanted twice. The residue was dried in vacuo to give the title compound (56 mg) as a white foam.

$^1$H-NMR (d$_6$-DMSO): δ (ppm) 9.44 (bm, 1H); 9.09 (bm, 1H); 7.94 (bs, 1H); 7.65 (bs, 2H); 7.32 (dd, 1H); 6.97 (dd, 1H); 6.88 (dt, 1H); 5.36 (dd, 1H); 4.93 (q, 1H); 3.94 (m, 1H); 3.77 (m, 1H); 3.63 (m, 1H); 3.28 (m, 2H), 2.97 (m, 1H); 2.47 (s, 3H); 2.34 (s, 3H); 2.06 (m, 1H); 1.88 (m, 1H); 1.50 (d, 3H).

MS (ES/+): m/z=506 [M+H−HCl]$^+$.

EXAMPLE 4

7-(R)-(4-Fluoro-2-methyl-phenyl)-[1,4]-diazepane-1-carboxylic acid, [1-(R)-(3,5-bis-trifluoromethyl-phenyl)-ethyl]-methylamide hydrochloride A solution of p-tosyl chloride (86 mg) in acetone (1.5 mL) was added drop-wise to a mixture of intermediate 14b (154 mg) in acetone (3 mL) and 5% sodium carbonate solution (3 mL) under a Nitrogen atmosphere. The mixture was stirred for 30 minutes at r.t. then it was heated to reflux for 1 hour.

The mixture was concentrated in vacuo to eliminate the acetone and the aqueous residue was extracted twice with DCM. The organic layer was dried and concentrated in vacuo to a residue which was purified by chromatography (AcOEt) to give 7-(R)-(4-fluoro-2-methyl-phenyl)-5-oxo-[1,4]diazepane-1-carboxylic acid, [1-(R)-(3,5-bis-trifluoromethyl-phenyl)-ethyl]-methylamide (90 mg) as a colourless oil.

Borane (1 M solution in THF-0.5 mL) was added drop-wise to a solution of 7-(R)-4-fluoro-2-methyl-phenyl)-5-oxo-[1,4]-diazepane-1-carboxylic acid, [1-(R)-(3,5-bis-trifluoromethyl-phenyl)-ethyl]-methylamide (90 mg) in anhydrous THF (5 mL) under a Nitrogen atmosphere. The mixture was heated to reflux for 2 hours. Then, the solution was cooled to 0° C. and a 6M hydrochloric acid solution (5 mL) was added. The mixture was allowed to warm to r.t. and stirred overnight. After concentration in vacuo to eliminate the THF, the aqueous residue was cooled to 0° C. and treated with solid sodium hydroxide until pH=9. The mixture was extracted with DCM (4×20 mL). The combined organic extracts were dried and concentrated in vacuo to a residue which was purified by flash chromatography (from AcOEt to AcOEt/MeOH 8:2) to give 7-(R)-(4-fluoro-2-methyl-phenyl)-[1,4]-diazepane-1-carboxylic acid, [1-(R)-(3,5-bis-trifluoromethyl-phenyl)-ethyl]-methylamide (48 mg).

This material was dissolved in dry Et$_2$O (1.2 mL) and treated with hydrochloric acid (1M in Et$_2$O-0.4 mL) at 0° C. The resulting solution was stirred at r.t. for 15 minutes, then pentane (3 mL) was added and decanted twice. The residue was dried in vacuo to give the title compound (40 mg) as a white foam.

$^1$H-NMR (d$_6$-DMSO): δ (ppm) 8.94 (bs, 2H); 7.96 (bs, 1H); 7.71 (bs, 2H); 7.3 (dd, 1H); 6.93 (m, 2H); 5.14 (dd, 1H); 4.92 (q, 1H); 4.01 (dd, 1H); 3.71 (dd, 1H); 3.4–3.12 (m, 4H); 2.44 (s, 3H); 2.24 (s, 3H); 2.25–2.1 (r, 2H); 1.51 (d, 3H).

MS (ES/+): m/z=506 [M+H−HCl]$^+$.

EXAMPLE 5

2-(S)-(4-Fluoro-2-methyl-phenyl)-[1,4]-diazepane-1-carboxylic acid, (3,5-dichloro-benzyl)-methylamide hydrochloride Borane (1 M solution in THF-0.8 mL) was added drop-wise to a solution of intermediate 17 (125 mg) in anhydrous THF (7 mL) under a Nitrogen atmosphere.

The mixture was heated to reflux for 2.5 hour. Then, the solution was cooled to 0° C. and a 6M hydrochloric acid solution (7 mL) was added. The mixture was allowed to warm to r.t. and stirred overnight. After concentration in vacuo to eliminate the THF, the aqueous solution was cooled to 0° C. and treated with solid sodium hydroxide until pH=9. The mixture was extracted with DCM (4×20 mL). The combined organic extracts were dried and concentrated in vacuo to a residue which was purified by chromatography (from AcOEt to AcOEt/MeOH 7:3) to give 2-(S)-(4-fluoro-2-methyl-phenyl)-[1,4]-diazepane-1-carboxylic acid, (3,5-dichloro-benzyl)-methylamide (70 mg).

This material was dissolved in dry $Et_2O$ (2 mL) and treated with hydrochloric acid (1M in $Et_2O$-0.24 mL) at 0° C. The resulting solution was stirred at r.t. for 15 minutes, then pentane (3 mL) was added and decanted twice. The residue was dried in vacuo to give the title compound (68.8 mg) as a white foam.

$^1$H-NMR ($d_6$-DMSO): δ (ppm) 9.11 (bs, 1H); 8.9 (bs, 1H); 7.38 (bs, 1H); 7.3 (dd, 1H); 6.95 (m, 2H); 6.88 (s, 2H); 5.29 (dd, 1H); 4.16 (s, 2H); 3.83 (dd, 1H); 3.71 (dd, 1H); 3.58 (t, 1H); 3.35–3.2 (m, 2H); 2.92 (t, 1H); 2.57 (s, 3H); 2.33 (s, 3H); 2.01 (m, 1H); 1.81 (m, 1H).

MS (ES/+): m/z=424 [M+H−HCl]$^+$.

EXAMPLE 6

7-(R)-(4-Fluoro-2-methyl-phenyl)-[1,4]-diazepane-1-carboxylic acid, (3,5-dichloro-benzyl)-methylamide hydrochloride Borane (1 M solution in THF-0.8 mL) was added drop-wise to a solution of intermediate 18 (125 mg) in anhydrous THF (7 mL) under a Nitrogen atmosphere.

The mixture was heated to reflux for 1.5 hour. Then, the solution was cooled to 0° C. and a 6M hydrochloric acid solution (6 mL) was added. The mixture was allowed to warm to r.t. and stirred for 4 hours. After concentration in vacuo to eliminate the THF, the aqueous residue was cooled to 0° C. and treated with solid sodium hydroxide until pH=9. The mixture was extracted with DCM (4×15 mL). The combined organic extracts were dried and concentrated in vacuo to a residue which was purified by flash chromatography (from AcOEt to AcOEt/MeOH 7:3) to give 7-(R)-(4-fluoro-2-methyl-phenyl)-[1,4]-diazepane-1-carboxylic acid, (3,5-dichloro-benzyl)-methylamide (22 mg).

This material was dissolved in dry $Et_2O$ (0.6 mL) and treated with hydrochloric acid (1M in $Et_2O$-0.07 mL) at 0° C. The resulting solution was stirred at r.t. for 15 minutes, then pentane (3 mL) was added and decanted twice. The residue was dried in vacuo to give the title compound (16 mg) as a white foam.

$^1$H-NMR ($d_6$-DMSO): δ (ppm) 8.9–8.7 (bs, 2H); 7.43 (s, 1H); 7.3 (m, 1H); 7.0 (s, 2H); 7.0–6.94 (m, 2H); 5.1 (dd, 1H); 4.18 (m, 2H); 3.94 (dd, 1H); 3.67 (dd, 1H); 3.4–3.1 (m, 4H); 2.63 (s, 3H); 2.27 (s, 3H); 2.22 (m, 1H); 2.1 (m, 1H).

MS (ES/+): m/z=424 [M+H−HCl]$^+$.

EXAMPLE 7

2-(S)-(4-Fluoro-2-methyl-phenyl)-[1,4]-diazepane-1-carboxylic acid, [1-(S)-(3,5-bis-trifluoromethyl-phenyl)-ethyl]-methylamide hydrochloride Borane (1 M solution in THF-0.633 mL) was added drop-wise to a solution of intermediate 20 (110 mg) in anhydrous THF (7 mL) under a Nitrogen atmosphere. The mixture was heated to reflux for 3 hours. Then, the solution was cooled to 0° C. and 6M hydrochloric acid solution (7 mL) was added. The mixture was allowed to warm to r.t. and stirred at r.t. overnight. The mixture was cooled to −8° C. and treated with solid sodium hydroxide until pH=9. The mixture was extracted with DCM (4×15 mL). The combined organic extracts were dried and concentrated in vacuo to a residue which was purified by flash chromatography (from AcOEt to AcOEt/MeOH 7:3) to give 2-(S)-(4-fluoro-2-methyl-phenyl)-[4,1]-diazepane-1-carboxylic acid, [1-(S)-3,5-bis-trifluoromethyl-phenyl)-ethyl]-methylamide (100 mg).

This material was dissolved in dry $Et_2O$ (2.5 mL) and treated with hydrochloric acid (1M in $Et_2O$-0.15 mL) at 0° C. The resulting solution was stirred at r.t. for 15 minutes, then pentane (3 mL) was added and decanted twice. The residue was dried in vacuo to give the title compound (87 mg) as a white foam.

IR (nujol, cm$^{-1}$): 1637 (C=O).

$^1$H-NMR ($d_6$-DMSO): δ (ppm) 9.2–8.8 (bs, 2H); 7.92 (s, 1H); 7.64 (s, 2H); 7.32 (t, 1H); 7.0–6.88 (m, 2H); 5.3 (d, 1H); 5.0 (q, 1H); 3.86 (m, 1H); 3.73 (m, 1H); 3.59 (m, 1H); 3.3 (m, 2H); 2.95 (m, 1H); 2.55 (s, 3H); 2.36 (s, 3H); 2.1–1.8 (m, 2H); 14.5 (d, 3H).

MS (ES/+): m/z=506 [M+H−HCl]$^+$.

EXAMPLE 8

7-(R)-(4-Fluoro-2-methyl-phenyl)-[1,4]-diazepane-1-carboxylic acid, [1-(S)-(3,5-bis-trifluoromethyl-phenyl)-ethyl]-methylamide hydrochloride Borane (1 M solution in THF-0.5 mL) was added drop-wise to a solution of intermediate 21 (82 mg) in anhydrous THF (4.5 mL) under a Nitrogen atmosphere.

The mixture was heated to reflux for 3 hours. Then, the solution was cooled to 0° C. and a 6M hydrochloric acid solution (5 mL) was added. The mixture was allowed to warm to r.t. and stirred at r.t. overnight. The mixture was cooled to −8° C. and treated with solid sodium hydroxide until pH=9. The mixture was extracted with DCM (4×15 mL). The combined organic extracts were dried and concentrated in vacuo to a residue which was purified by flash chromatography (from AcOEt to AcOEt/MeOH 7:3) to give 7-(R)-(4-fluoro-2-methyl-phenyl)-[1,4]-diazepane-1-carboxylic acid, [1-(S)-(3,5-bis-trifluoromethyl-phenyl)-ethyl]-methylamide (33 mg).

This material was dissolved in dry $Et_2O$ (0.75 mL) and treated with hydrochloric acid (1M in $Et_2O$-0.1 mL) at 0° C. The resulting solution was stirred at r.t. for 15 minutes, then pentane (3 mL) was added and decanted twice. The residue was dried in vacuo to give the title compound (34 mg) as a white foam.

IR (nujol, cm$^{-1}$): 3398 (NH), 1637 (C=O).

$^1$H-NMR ($d_6$-DMSO): δ (ppm) 8.85–8.65 (bs, 2H); 7.94 (s, 1H); 7.72 (s, 2H); 7.34 (dd, 1H); 6.98 (dd, 1H); 6.91 (dt, 1H); 5.13 (dd, 1H); 5.06 (q, 1H); 3.83 (dd, 1H); 3.64 (dd, 1H); 3.5–3.3 (m, 2H); 3.17 (m, 2H); 2.57 (s, 3H); 2.22–2.11 (m, 2H); 2.28 (s, 3H); 1.43 (d, 3H).

MS (ES/+): m/z=506 [M+H−HCl]$^+$.

EXAMPLE 9

2-(S)-(4-Fluoro-2-methyl-phenyl)-[1,4]-diazepane-1-carboxylic acid, (3-chloro-4-fluoro-benzyl)methyla-mide hydrochloride A solution of p-tosyl chloride (109 mg) in acetone (1.9 mL) was added drop-wise to a mixture of intermediate 23a (160 mg) in acetone (3.8 mL) and 5% sodium carbonate solution (3.8 mL) under a Nitrogen atmosphere. The mixture was stirred at room temperature for 15 minutes, then it was heated to reflux for 45 minutes. The mixture was allowed to cool to r.t., and the aqueous residue was extracted with DCM. The organic layer was washed with a 5% sodium hydrogen carbonate solution (10 mL). The aqueous phase was re-extracted with DCM (3×20 mL). The combined organic extracts were dried and concentrated in vacuo to give the crude 2-(S)-(4-fluoro-2-methyl-phenyl)-5-oxo-[1,4]-diazepane-1-carboxylic acid, 3-chloro-4-fluoromethyl-benzyl)-methylamide (135 mg-T.l.c.: AcOEt 100%, Rf=0.15).

Borane (1 M solution in THF-1.3 mL) was added drop-wise to a solution of this compound (135 mg) in anhydrous THF (10.5 mL) under a Nitrogen atmosphere.

The mixture was heated to reflux for 3 hours. Then, the solution was cooled to 0° C. and a 6M hydrochloric acid solution (7 mL) was added. The mixture was allowed to warm to r.t. and stirred at r.t. overnight. The mixture was cooled to −8° C. and treated with solid sodium hydroxide until pH=9. The mixture was extracted with DCM (4×15 mL). The combined organic extracts were dried and concentrated in vacuo to a residue which was purified by flash chromatography (from AcOEt to AcOEt/MeOH 9:1) to give 2-(S)-(4-fluoro-2-methyl-phenyl)-[1,4]-diazepane-1-carboxylic acid, (3-chloro-5-fluoromethyl-benzyl)-methylamide (61 mg).

This material was dissolved in dry $Et_2O$ (1.7 mL) and treated with hydrochloric acid (1M in $Et_2O$-0.2 mL) at 0° C. The resulting solution was stirred at r.t. for 15 minutes, then pentane (3 mL) was added and decanted twice. The residue was dried in vacuo to give the title compound (65 mg) as a white foam.

IR (nujol, $cm^{-1}$): 3406 (NH2); 1629 (C=O).
$^1$H-NMR ($d_6$-DMSO): δ (ppm) 9.15–8.9 (2bs, 2H); 7.34 (t, 1H); 7.25 (t, 1H); 7.05–6.95 (m, 4H); 5.33 (dd, 1H); 4.17 (q, 2H); 3.9 (dd, 1H); 3.7 (dd, 1H); 3.6 (m, 1H); 3.35–3.2 (m, 2H); 2.95 (m, 1H); 2.58 (s, 3H); 2.36 (s, 3H); 2.02 (m, 1H); 1.85 (m, 1H).
MS (ES/+): m/z=408 [M+H−HCl]$^+$.

EXAMPLE 10

7-(R)-(4-Fluoro-2-methyl-phenyl)-[1,4]-diazepane-1-carboxylic acid, (3-chloro-4-fluoro-benzyl)-methylamide hydrochloride A solution of p-tosyl chloride (75 mg) in acetone (1.2 mL) was added drop-wise to a mixture of intermediate 23b (110 mg) in acetone (2.6 mL) and 5% sodium carbonate solution (2.6 mL) under a Nitrogen atmosphere. The mixture was stirred at room temperature for 15 minutes, then it was heated to reflux for 45 minutes. The mixture was allowed to cool to r.t., and the aqueous residue was extracted with DCM. The organic layer was washed with a 5% sodium hydrogen carbonate solution (10 mL). The aqueous phase was re-extracted with DCM (3×20 mL). The combined organic extracts were dried and concentrated in vacuo to give the crude 7-(R)-(4-fluoro-2-methyl-phenyl)-5-oxo-[1,4]-diazepane-1-carboxylic acid, (3-chloro-4-fluoromethyl-benzyl)-methylamide (91 mg-T.l.c.: AcOEt 100%, Rf=0.16).

Borane (1 M solution in THF-0.9 mL) was added drop-wise to a solution of this compound (91 mg) in anhydrous THF (7.2 mL) under a nitrogen atmosphere. The mixture was heated to reflux for 3 hours. Then, the solution was cooled to 0° C. and a 6M hydrochloric acid solution (7 mL) was added. The mixture was allowed to warm to r.t. and stirred at r.t. overnight. The mixture was cooled to −8° C. and treated with solid sodium hydroxide until pH=9. The mixture was extracted with DCM (4×15 mL). The combined organic extracts were dried and concentrated in vacuo to a residue which was purified by flash chromatography (from AcOEt to AcOEt/MeOH 7:3) to give 7-(R)-4-fluoro-2-methyl-phenyl)-[1,4]-diazepane-1-carboxylic acid, (3-chloro-5-fluoromethyl-benzyl)-methylamide (36 mg).

This material was dissolved in dry $Et_2O$ (1.2 mL) and treated with hydrochloric acid (1M in $Et_2O$-0.1 mL) at 0° C. The resulting solution was stirred at r.t. for 15 minutes, then pentane (3 mL) was added and decanted twice. The residue was dried in vacuo to give the title compound (35 mg) as a white foam.

IR (nujol, $cm^{-1}$): 3471 and 3411 (NH2); 1625 (C=O).
$^1$H-NMR ($d_6$-DMSO): δ (ppm) 8.8–8.7 (2bs, 2H); 7.27 (m, 1H); 7.3 (dd, 1H); 7.12 (dd, 1H); 7.06 (d, 1H); 7.0–6.9 (m, 2H); 5.09 (dd, 1H); 4.24–4.08 (dd, 2H; 3.95 (dd, 1H); 3.65 (dd, 1H); 3.4–3.1 (m, 4H); 2.6 (s, 3H); 2.26 (s, 3H); 2.25–2.05 (m, 2H).
MS (ES/+): m/z=408 [M+H−HCl]$^+$.

EXAMPLE 11

7-(R)-(4-Fluoro-2-methyl-phenyl)-[1,4]-diazepane-1-carboxylic acid, (2,5-dichloro-benzyl)-methylamide hydrochloride A solution of p-tosyl chloride (28 mg) in acetone (0.5 mL) was added drop-wise to a mixture of intermediate 25b (43 mg) in acetone (1 mL) and 5% sodium carbonate solution (1 mL) under a Nitrogen atmosphere. The mixture was stirred at room temperature for 15 minutes, then it was heated to reflux for 45 minutes. The mixture was allowed to cool to r.t., and the aqueous residue was extracted with DCM. The organic layer was washed with a 5% sodium hydrogen carbonate solution (10 mL). The aqueous phase was re-extracted with DCM (3×20 mL). The combined organic extracts were dried and concentrated in vacuo to give the crude 7-(R)-4-fluoro-2-methyl-phenyl)-5-oxo-[1,4]-diazepane-1-carboxylic acid, (2,5-dichloro-benzyl)-methylamide (38 mg).

Borane (1 M solution in THF-0.35 mL) was added drop-wise to a solution of this compound (38 mg) in anhydrous THF (3 mL) under a Nitrogen atmosphere. The mixture was heated to reflux for 4 hours. Then, the solution was cooled to 0° C. and a 6M hydrochloric acid solution (3 mL) was added. The mixture was allowed to warm to r.t. and stirred at r.t. overnight. The mixture was cooled to −8° C. and treated with solid sodium hydroxide until pH=9. The mixture was extracted with DCM (4×15 mL). The combined organic extracts were dried and concentrated in vacuo to a residue which was purified by flash chromatography (from AcOEt to AcOEt/MeOH 9:1) to give 7-(R)-(4-fluoro-2-methyl-phenyl)-[1,4]-diazepane-1-carboxylic acid, (2,5-dichloro-benzyl)-methylamide (23 mg).

This material was dissolved in dry $Et_2O$ (0.7 mL) and treated with hydrochloric acid (1M in $Et_2O$-0.1 mL) at 0° C. The resulting solution was stirred at r.t. for 15 minutes, then pentane (0.5 mL) was added and decanted twice. The residue was dried in vacuo to give the title compound (18 mg) as a white foam.

$^1$H-NMR ($d_6$-DMSO): δ (ppm) 8.8–8.6 (2bs, 2H); 7.38 (m, 1H); 7.3 (m, 2H); 7.02 (d, 1H); 6.92 (m, 2H); 4.99 (m, 1H); 4.22 (d, 1H); 4.66 (d, 1H); 3.89 (dd, 1H); 3.63 (dd, 1H);

3.16 (m, 1H); 3.06 (m, 1H); 3.5–3.3 (m, 2H); 2.65 (s, 3H); 2.23 (m, 1H); 2.13 (s, 3H); 1.99 (m, 1H).
MS (ES/+): m/z=424 [M+H−HCl]$^+$.

EXAMPLE 12

2-(S)-(4-Fluoro-phenyl)-[1,4]-diazepane-1-carboxylic acid, (3,5bis-trifluoromethyl-benzyl)-methylamide hydrochloride (12a)

7-(R)-(4-Fluoro-phenyl)-[1,4]-diazepane-1-carboxylic acid, (3,5-bis-trifluoromethyl-benzyl)-methylamide hydrochloride (12b)

Hydroxylamine hydrochloride (535 mg), sodium acetate (632 mg) and dry magnesium sulphate (500 mg) were added to a solution of intermediate 30 (370 mg) in dry MeOH (23 mL) under a Nitrogen atmosphere.

The mixture was stirred at r.t. for 6 hours, then it was filtered over celite washing with AcOEt. The organic layer was washed with brine, dried and concentrated in vacuo to a mixture of (E)-2-(R)-(4-fluoro-phenyl)-4-hydroxyimino-piperidine-1-carboxylic acid (3,5-bis-trifluoromethyl-benzyl)-methylamide and (Z)-2-(R)-(4-fluoro-phenyl)-4-hydroxyimino-piperidine-1-carboxylic acid, (3,5-bis-trifluoromethyl-benzyl)-methylamide (274 mg) which was used without purification for the next reaction.

A solution of p-tosyl chloride (160 mg) in acetone (2.8 mL) was added drop-wise to a mixture of the intermediates previously described (274 mg) in acetone (5.6 mL) and 5% sodium carbonate solution (5.6 mL) under a Nitrogen atmosphere. The mixture was stirred at r.t. for 15 minutes, then it was heated to reflux for 45 minutes. The mixture was allowed to cool to r.t., concentrated in vacuo to eliminate the acetone and the aqueous residue was extracted with DCM. The organic layer was washed with a 5% sodium hydrogen carbonate solution (20 mL). The aqueous phase was re-extracted with DCM (3×20 mL). The combined organic extracts were dried and concentrated in vacuo. The residue was purified by flash chromatography (from CH/AcOEt 1:1 to AcOEt/MeOH 9:1) to give a mixture of 2-(S)-(4-fluoro-phenyl)-5-oxo-[1,4]-diazepane-1-carboxylic acid, (3,5-bis-trifluoromethyl-benzyl)-methylamide and 7-(R)-(4-fluoro-phenyl)-5-oxo-[1,4]-diazepane-1-carboxylic acid, (3,5-bis-trifluoromethyl-benzyl)-methylamide (210 mg).

Borane (1 M solution in THF-1.71 mL) was added drop-wise to a solution of the intermediates previously described (210 mg) in anhydrous THF (14 mL) under a Nitrogen atmosphere.

The mixture was heated to reflux for 1.5 hours. Then, the solution was cooled to 0° C. and hydrochloric acid (6M solution −10 mL) was added. The mixture was allowed to warm to r.t. and stirred at r.t. overnight. The solution was cooled to 0° C. and treated with solid sodium hydroxide until pH=9. The mixture was extracted with DCM (4×15 mL). The combined organic extracts were washed with brine (20 mL), dried and concentrated in vacuo to a residue which was purified by chromatography (from AcOEt 100% to AcOEt/MeOH 1:1) to give two fractions:
1. 2-(S)-(4-fluoro-phenyl)-[1,4]-diazepane-1-carboxylic acid, (3,5-bis-trifluoromethyl-benzyl)-methylamide (71 mg-T.l.c.: AcOEt/MeOH 1:1, Rf=0.34), named compound 1;
2. 7-(R)-(4-fluoro-phenyl)-[1,4]-diazepane-1-carboxylic acid, (3,5-bis-trifluoromethyl-benzyl)-methylamide (64 mg-T.l.c.: AcOEt/MeOH 1:1, Rf=0.17), named compound 2.

EXAMPLE 12a

Compound 1 (71 mg) was dissolved in dry Et2O (1.5 mL) and treated with hydrochloric acid (1M in Et$_2$O-0.2 mL) at 0° C. The resulting solution was stirred at r.t. for 15 minutes, then pentane (3 mL) was added and decanted twice. The residue was dried in vacuo to give the title compound (71 mg) as a white foam.
$^1$H-NMR (d$_6$-DMSO): δ (ppm) 9.09 (bs, 1H); 8.76 (bs, 1H); 7.95 (s, 1H); 7.71 (m, 2H); 7.3 (dd, 2H); 7.11 (t, 2H); 5.16 (dd, 1H); 4.37 (m, 2H); 3.9 (m, 1H); 3.7 (m, 2H); 3.5 (m, 1H); 3.3 (m, 1H); 3.0 (m, 1H); 2.68 (s, 3H); 2.0–1.9 (m, 2H).
MS (ES/+): m/z=478 [M+H−HCl]$^+$.

EXAMPLE 12b

Compound 2 (64 mg) was dissolved in dry Et$_2$O (1.5 mL) and treated with hydrochloric acid (1M in Et$_2$O-0.2 mL) at 0° C. The resulting solution was stirred at r.t. for 15 minutes, then pentane (3 mL) was added and decanted twice. The residue was dried in vacuo to give the title compound (64 mg) as a white solid.
$^1$H-NMR (d$_6$-DMSO): δ (ppm) 8.73 (bs, 1H); 8.51 (bs, 1H); 7.96 (s, 1H); 7.77 (m, 2H); 7.26 (dd, 2H); 7.1 (m, 2H;); 5.06 (dd, 1H); 4.39 (m, 2H); 3.98 (dd, 1H); 3.5–3.0 (m, 4H); 2.7 (s, 3H); 2.45 (m, 1H); 2.08 (m, 1H).
MS (ES/+): m/z=478 [M+H−HCl]$^+$.

EXAMPLE 13

7-(R)-(4-Fluoro-2-methyl-phenyl)-4-methyl-[1,4]-diazepane-1-carboxylic acid, (3,5-dichloro-benzyl)-methylamide hydrochloride A mixture of example 6 (51 mg), aqueous formaldehyde (33 μL) and sodium triacetoxyacetoxyborohydride (50 mg) in anhydrous 1,2-dichloroethane (2 mL) was stirred at r.t. overnight. The mixture was washed with water (2 mL) and brine (2 mL) and concentrated in vacuo. The residue was purified by flash chromatography (AcOEt 100%) to give 7-(R)-(4-fluoro-2-methyl-phenyl)-4-methyl-[1,4]-diazepane-1-carboxylic acid, (3,5-dichloro-benzyl)-methylamide (10 mg).

This material (10 mg) was dissolved in dry Et$_2$O (1.5 mL) and treated with hydrochloric acid (1M in Et$_2$O-0.3 mL) at 0° C. The resulting solution was stirred at r.t. for 15 minutes, then pentane (2 mL) was added and decanted twice. The residue was dried in vacuo to give the title compound (10 mg) as a white solid.
$^1$H-NMR (d$_6$-DMSO): δ (ppm) 10.09 (bs, 1H); 7.47–7.23 (dd, 1H); 7.4 (s, 1H); 6.93 (m, 4H); 5.08 (m, 1H); 4.27–4.09 (2d, 2H); 4.01–3.76 (dd, 2H); 3.7–3.1 (m, 3H); 2.8–2.57 (2s, 3H); 2.77 (2d, 3H); 2.27–2.24 (s, 3H); 2.3–1.9 (m, 2H).

EXAMPLE 14

7-(R)-(4-Fluoro-2-methyl-phenyl)-4-methyl-[1,4]-diazepane-1-carboxylic acid, (3,5-bis-trifluoromethyl-benzyl)-methylamide hydrochloride A mixture of example 2 (53 mg), aqueous formaldehyde (33 μL) and sodium triacetoxyacetoxyborohydride (50 mg) in anhydrous 1,2-dichloroethane (2 mL) was stirred at r.t. overnight. The mixture was washed with water (2 mL) and brine (2 mL) and concentrated in vacuo. The residue was purified by flash chromatography (AcOEt 100%) to give 7-(R)-(4-fluoro-2-methyl-phenyl)-4-methyl-[1,4]-diazepane-1-carboxylic acid, (3,5-bis-trifluoromethyl-benzyl)-methylamide (12 mg).

This material (12 mg) was dissolved in dry $Et_2O$ (1.5 mL) and treated with hydrochloric acid (1M in $Et_2O$-0.3 mL) at 0° C. The resulting solution was stirred at r.t. for 15 minutes, then pentane (2 mL) was added and decanted twice. The residue was dried in vacuo to give the title compound (11.5 mg) as a white solid.

$^1$H-NMR ($d_6$-DMSO): δ (ppm) 10.3–10.19 (2bs, 1H); 7.94 (bs, 1H); 7.69–7.63 (2bs, 2H); 7.53–7.26 (2dd, 1H); 6.91 (m, 2H); 5.13 (m, 1H); 4.53–4.33 (2d, 2H); 4.03–3.83 (dd, 1H); 3.7–3.2 (m, 4H); 2.84–2.64 (2s, 3H); 2.81 (2d, 3H); 2.29–2,25 (2s, 3H); 2.35–1.9 (m, 2H).

EXAMPLE 15

7-(R)-(4-Fluoro-2-methyl-phenyl)-4-methyl-[1,4]-diazepane-1-carboxylic acid, [1-(R)-(3,5-bis-trifluoromethyl-phenyl)-ethyl]-methylamide hydrochloride.

A mixture of example 4 (10 mg), aqueous formaldehyde (29 µL) and 10% Pd/C (5 mg) in anhydrous MeOH (1 mL) was hydrogenated at r.t. and Patm. for 1 hour. The mixture was filtered and the organic layer was concentrated in vacuo. The residue was triturated with Et2O/pentane to give the title compound (5 mg) as a whitish solid.

$^1$H-NMR ($d_6$-DMSO): δ (ppm) 10.4 (bs, 1H); 7.95 (s, 1H); 7.66 (s, 2H); 7.26 (m, 1H); 7.0–6.8 (m, 2H); 5.15 (dd, 1H); 4.89 (q, 1H); 4.05–3.8 (m, 2H); 3.5–3.2 (m, 4H); 2.8 (s, 3H); 2.43 (s, 3H); 2.22 (s, 3H); 2.21 (m, 2H); 1.49 (d, 3H).

Pharmacy Examples

A. Capsules/Tablets

| | |
|---|---|
| Active ingredient | 20.0 mg |
| Starch 1500 | 2.5 mg |
| Microcrystalline Cellulose | 200.0 mg |
| Croscarmellose Sodium | 6.0 mg |
| Magnesium Stearate | 1.5 mg |

The active ingredient is blended with the other excipients. The blend can be used to fill gelatin capsules or compressed to form tablets using appropriate punches. The tablets can be coated using conventional techniques and coatings.

| B. Tablets | |
|---|---|
| Active ingredient | 20.0 mg |
| Lactose | 200.0 mg |
| Microcrystalline Cellulose | 70.0 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| C. Bolus | |
|---|---|
| Active ingredient | 2–60 mg/ml |
| Sodium phosphate | 1.0–50.0 mg/ml |
| water for injection | qs to 1 ml |

The formulation may be packed in glass ampoules or vials and syringes with a rubber stopper and a plastic/metal overseal (vials only).

| D. Infusion | |
|---|---|
| Active ingredient | 2–60 mg/ml |
| Infusion solution (NaCl 0.9% or 5% dextrose) | qs to 100 ml |

The formulation may be packed in glass vials or plastic bag.

The affinity of the compound of the invention for NK1 receptor was determined using the $NK_1$-receptor binding affinity method measuring in vitro by the compounds' ability to displace [3H]-substance P (SP) from recombinant human $NK_1$ receptors expressed in Chinese Hamster Ovary (CHO) cell membranes. The affinity values are expressed as negative logarithm of the inhibition constant (Ki) of displacer ligands (pKi).

The pKi values obtained as the average of at least two determinations with representative compounds of the invention are given in the following table:

| Example No | Pki |
|---|---|
| 1 | 10.46 |
| 2 | 10.14 |
| 3 | 10.61 |
| 4 | 10.71 |
| 5 | 10.18 |
| 6 | 10.01 |
| 7 | 10.32 |
| 8 | 10.34 |
| 12a | 9.30 |
| 13 | 9.53 |
| 14 | 10.25 |
| 15 | 10.51 |

What is claimed is:

1. A compound of formula (I)

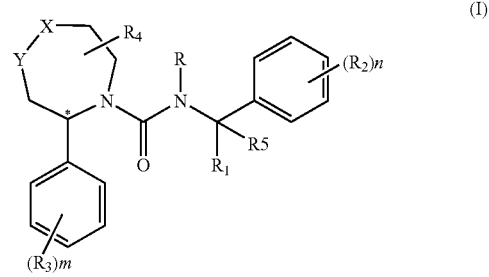

wherein

R is hydrogen or $C_{1-4}$ alkyl;

$R_1$ is hydrogen or $C_{1-4}$ alkyl;

$R_2$ is trifluoromethyl, $C_{1-4}$ alkyl, $C_{1-4}$ alkoxy, trifluoromethoxy or halogen;

$R_3$ is halogen $C_{1-4}$ alkyl;

$R_4$ is hydrogen, halogen, $C_{1-4}$ alkyl or $C(O)R_6$;

$R_5$ is hydrogen, $C_{1-4}$ alkyl or $R_5$ together within the $R_1$ represents $C_{3-7}$ cycloalkyl;

$R_6$ is hydroxy, amino, methylamino, dimethylamino, 5 membered heteroaryl group containing 1 to 3 heteroatoms selected independently from oxygen, sulphur and nitrogen or a 6 membered heteroaryl group containing 1 to 3 nitrogen atoms;

m or n are independently zero or an integer from 1 to 3;

X and Y are independently $NR_7$ or methylene;

$R_7$ is hydrogen, $C_{1-4}$ alkyl or $C_{3-7}$ cycloalkyl;

provided that when X is $NR_7$, Y is methylene and when X is methylene, Y is $NR_7$;

or a pharmaceutically acceptable salt or solvate thereof.

2. A compound as claimed in claim 1 wherein the chiral atom indicated as * is in β configuration.

3. A compound as claimed in claim 1 wherein m is 2 and the groups $R_3$ are at the 2 and the 4 positions of the phenyl ring.

4. A compound as claimed in claim 1 wherein $R_2$ is trifluoromethyl or halogen, $R_3$ is halogen or $C_{1-4}$ alkyl at the 2 and the 4 position of the phenyl ring, X is NH and Y is methylene or Y is NH and X is methylene, $R_1$ is a methyl or hydrogen, R is methyl, $R_5$ and $R_4$ are hydrogen, m is 2 and n is 1 or 2.

5. A pharmaceutical composition comprising a compound as claimed in claim 1 in a mixture with one or more pharmaceutically acceptable carriers or excipients.

6. A process for the preparation of a compound as claimed in claim 1, wherein Y is methylene and X is $NR_7$, which comprises reduction of a compound of formula (II) in which X is $NR_7$ with a suitable metal reducing agent,

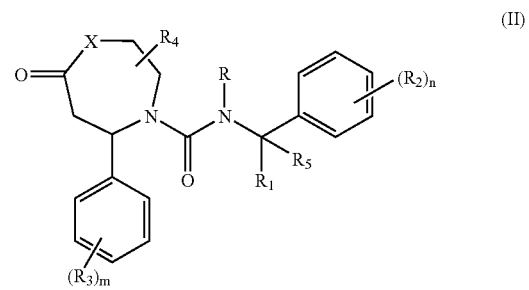

(II)

a process for the preparation of a compound as claimed in claim 1, wherein X is methylene and Y is $NR_7$, which comprises reduction of a compound of formula (III) in which Y is $NR_7$, with a suitable metal reducing agent,

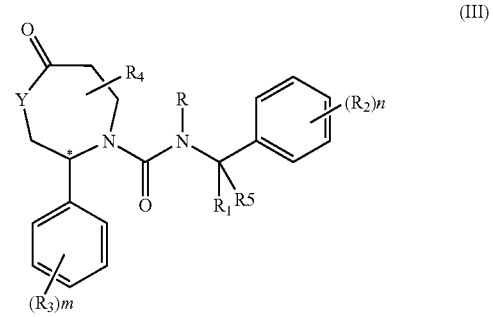

(III)

followed where necessary or desired by one or more of the following steps:
  i) separation of a compound of formula (I) into the enantiomers thereof;
  ii) isolation of the compound as a salt or a solvate thereof.

7. A method for the treatment of a condition selected from depressive states, anxiety, traumatic pain, cognitive disorders, emesis and gastrointestinal disorders in a mammal in need thereof, comprising administering an effective amount of a compound as claimed in claim 1.

8. The method as claimed in claim 7, wherein said mammal is man.

* * * * *